US008691551B1

(12) United States Patent
Lahtinen et al.

(10) Patent No.: US 8,691,551 B1
(45) Date of Patent: Apr. 8, 2014

(54) METHOD FOR RECOVERING PHOSPHORUS FROM ORGANIC MATERIALS

(71) Applicant: Ductor Oy, Helsinki (FI)

(72) Inventors: Minna Lahtinen, Espoo (FI); Elisa Lensu, Espoo (FI); Laura Tolvanen, Rajamäki (FI); Ilona Oksanen, Hensinki (FI); Juha Karjalainen, Hämeenlinna (FI)

(73) Assignee: Ductor Oy, Helsinki (FI)

( * ) Notice: Subject to any disclaimer, the term of this patent is extended or adjusted under 35 U.S.C. 154(b) by 0 days.

(21) Appl. No.: 14/066,299

(22) Filed: Oct. 29, 2013

Related U.S. Application Data

(60) Provisional application No. 61/790,927, filed on Mar. 15, 2013.

(51) Int. Cl.
*C12N 1/00* (2006.01)
(52) U.S. Cl.
USPC .......................................................... 435/243
(58) Field of Classification Search
CPC .............. C12N 1/00; C12N 1/20; C12N 1/04; A61K 38/00; C02F 3/34
USPC ....................................................... 435/243
See application file for complete search history.

(56) References Cited

U.S. PATENT DOCUMENTS 6,464,875 B1  10/2002  Woodruff
6,776,816 B1   8/2004  Ringelberg

FOREIGN PATENT DOCUMENTS

CN   102020508 A    4/2011
EP     1964828 B1   10/2008

OTHER PUBLICATIONS

Chen, G.J., Russell, J.B. 1989. More monensin-sensitive, ammonia-producing bacteria from the rumen. *Appl. Environ. Microbiol.* 55, 1052-1057.
Dowd, S.E., Wolcott, R.D., Sun, Y., McKeehan, T., Smith, E., Rhoads, D. 2008a. Polymicrobial nature of chronic diabetic foot ulcer biofilm infections determined using bacterial tag encoded FLX amplicon pyrosequencing (bTEFAP), *PLoS One* 3(10): e3326.
Dowd, S.E., Sun, Y., Secor, P.R., Rhoads, D.D., Wolcott, B.M., James, C.A., Wolcott, R.D. 2008b. Survey of bacterial diversity in chronic wounds using Pyrosequencing, DGGE, and full ribosome shotgun sequencing, *BMC Microbiology* 8: 43.
EC. 2009. Regulation (EC) No. 1069/2009 of the European Parliament and of the Council of Oct. 21, 2009 laying down health rules as regards animal by-products and derived products not intended for human consumption and repealing Regulation (EC) No. 1774/2002 (Animal by-products Regulation). *Off. J. Eur. Union* L300: 1-33.
Eschenlauer, S.C.P., McKain, N., Walker, N.D., McEwan, N.R., Newbold, C.J., Wallace, R.J. 2002. Ammonia production by ruminal microorganisms and enumeratin, isolation, and characterization of bacteria capable of growth on peptides and amino acids from the sheep rumen.*Appl. Environ. Microbiol.* 68(10): 4925-4931.
EU. 2011. Commission regulation (EU) No. 142/2011 of Feb. 25, 2011 implementing Regulation (EC) No. 1069/2009 of the European Parliament and of the Council laying down health rules as regards animal by-products and derived products not intended for human consumption and implementing Council Directive 97/78/EC as regards certain samples and items exempt from veterinary checks at the border under that Directive, *Off. J. Eur. Union* L54: 1-354.
Fouts, D.E., Szpakowski, S., Purushe, J., Torralba, M., Waterman, R.C., MacNeil, M.D., Alexander, L.J., Nelson, K.E. 2012. Next generation sequencing to define prokaryotic and fungal diversity in the bovine rumen. *PLoS One* 7(11): e48289.
Krause, D.O., Russell, J.B. 1996. An rRNA approach for assessing the role of obligate amino acid-fermenting bacteria in ruminal amino acid deamination. *Appl. Environ. Microbiol.* 62, 815-821.
Russell, J.B., Strobel, H.J., Chen, G.J. 1988. Enrichment and isolation of a ruminal bacterium with a very high specific activity of ammonia production. *Appl. Environ. Microbiol.* 54, 872-877.
Wolcott, R., Gontcharova, V., Sun, Y., Dowd, S.E. 2009, Evaluation of the bacterial diversity among and within individual venous leg ulcers using bacterial tag-encoded FLX and Titanium amplicon pyrosequencing and metagenomic approaches. *BMC Microbiology* 9: 226.

*Primary Examiner* — Karen Cochrane Carlson
*Assistant Examiner* — Jennifer M Tichy
(74) *Attorney, Agent, or Firm* — Robert P. Michal; Lucas and Marchanti, LLP

(57) ABSTRACT

The invention provides a process for producing phosphate from an organic material, the method including the steps of (a) fermenting an organic material in a medium in the presence of at least one microorganism, wherein the fermenting is under conditions, and for a sufficient period of time, to produce a fermentation product;
(b) treating the solids of the fermentation product with acid, in a medium, e.g., aqueous medium, to solubilize phosphates from the fermentation product; wherein the organic material, and thus the solids of the fermentation product, includes bone suitable for extraction of phosphates.

20 Claims, 5 Drawing Sheets

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial
<220> FEATURE:
<223> OTHER INFORMATION: Universal 16S RNA Bacteria Primer
<220> FEATURE:
<221> NAME/KEY: misc_feature
<222> LOCATION: (11)..(11)
<223> OTHER INFORMATION: n is a, c, g, or t

<400> SEQUENCE: 1
gagtttgatc ntggctcag                                               19

<210> SEQ ID NO 2
<211> LENGTH: 18
<212> TYPE: DNA
<213> ORGANISM: Artificial
<220> FEATURE:
```

-continued

```
<223> OTHER INFORMATION: Universal 16S RNA Bacteria Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (14)..(14)
<223> OTHER INFORMATION: k is t or g

<400> SEQUENCE: 2
gtnttacngc ggckgctg                                             18
```

METHOD FOR RECOVERING PHOSPHORUS FROM ORGANIC MATERIALS

TECHNICAL FIELD

The present invention relates generally to new processes for producing or recovering phosphorous compounds, such as phosphates, from organic raw materials by a process employing microbial fermentation and acid solubilization.

BACKGROUND OF THE INVENTION

Bone consists of inorganic minerals and organic substances. The inorganic minerals are formed from hydroxyapatite, $Ca_{10}(PO_4)_6(OH)_2$. The organic substances consist mainly of proteins, and the proteins consist mainly of collagen. To release phosphorus containing compounds e.g., phosphates, from bone, bone materials can be treated with acid in an aqueous medium, which solubilizes hydroxyapatite, resulting in the release of calcium ($Ca^{2+}$) and phosphate ($PO_4^{3-}$) ions into the aqueous medium (reaction equation 1). The presence of the bone protein matrix increases the amount of acid required, which increases both the size of the process equipment and the cost of mineral extraction, according to the following general reaction scheme.

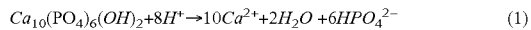

$$Ca_{10}(PO_4)_6(OH)_2 + 8H^+ \rightarrow 10Ca^{2+} + 2H_2O + 6HPO_4^{2-} \qquad (1)$$

Phosphorus containing compounds such as phosphates are important, for example, tor producing agricultural fertilizers. Currently the manufacture of phosphorous fertilizer requires manufacturing of an acid and then reacting the acid with certain bases in order to generate at fertlizer salt, such as ammonium phosphate, potassium phosphate etc.

European patent application EP1964828B1 discloses is method of using certain bacteria to generate reduced forms of phosphorus, such as phosphites and/or hyposphosphites from inorganic materials, such as rock phosphate and soils. U.S. Pat. No. 6,464,875 describes fermenting animal by-products to produce ammonia and solid materials for fertilizer production. CN102020508A relates to preparing a fertilizer by fermenting with "phosphorus-solubilizing bacterium" e.g. donkey bone and other organic material. The process includes a pre-fermenting step wherein the organic material is hydrolysed with a strong base. U.S. Pat. No. 6,776,816 describes production of magnesium ammonium phosphate by fermenting manure.

Nevertheless, there remains a longstanding need in the art for improved processes for phosphate production from food production byproducts and agricultural waste.

SUMMARY OF THE INVENTION

Accordingly, the invention provides a process for producing phosphates from an organic material, the method comprising:

(a) fermenting an organic material in a medium in the presence of at least one microorganism, wherein the fermenting is under conditions, and for a sufficient period of time, to produce a fermentation product;

(b) treating solids of the fermentation product with acid, in a medium to solubilize phosphates from the fermentation product;

wherein the organic material, and thus the solids of the fermentation product, comprises bone suitable for extraction of phosphates.

In a preferred embodiment, the medium is an aqueous medium.

In one embodiment, the fermentation process is conducted with an organic material ranging in density from 10 to 50 g/100 ml (wt/vol) of aqueous medium or more preferably, with an organic material ranging in density from 20 to 40, g/100 ml (wt/vol) of aqueous medium.

In an optional embodiment, the at least one microorganism is a bacteria capable of ammonification, and the process includes co-producing ammonia or ammonium during fermenting step (a). Preferably, the at least one at least one microorganism is as mixed bacterial population that has a correlation coefficient that is substantially similar to a mixed bacterial population of S1, FI1 or FO2. More preferably, the mixed bacterial population has a correlation coefficient of at least 0.90 relative to a mixed bacterial population of S1, HI or FO2, or alternatively, the mixed bacterial population has a correlation coefficient of at least 0.95, relative to a mixed bacterial population of S1, FI1 or FO2.

In a preferred embodiment, the acid is an organic acid or an inorganic acid, for example, tartaric acid, malic acid, citric acid, sulfuric acid and/or combinations thereof.

The inventive process optionally further includes the steps of:

separating a liquid phase from the acid treated fermentation product, admixing a reagent comprising $NH_4^+$ and/or a reagent comprising $Mg^{2+}$ ions into the separated liquid phase in a sufficient amount and for a period of time sufficient to precipitate solubilized phosphates from the separated liquid phase, and recovering the precipitated phosphate.

Preferably, the precipitated phosphate is struvite or magnesium ammonium phosphate, formed by the reaction $Mg^{2+} + NH_4^+ + PO_4^{3-} + 6H_2O \rightarrow MgNH_4PO_4 \cdot 6_2O$.

Preferably, the fermenting step (a) is conducted with an inoculum of microorganisms ranging in dose from 1 to 20 (vol-%) or more preferably with an inoculum of microorganisms ranging in dose from 5 to 10 vol-%.) Preferably, the fermenting step (a) is conducted at a temperature ranging from 30 to 60° C. or more preferably the fermenting step is conducted at a temperature ranging from 40 to 55° C. Preferably, the fermenting step (a) is conducted for a time ranging from 10 hours to 7 days, or more preferably, the fermenting step is conducted for a time ranging from 12 hours to 18 hours.

Preferably, the acid solubilizing step (b) is conducted at a pH ranging from 1 to 6 or more preferably from a pH ranging from 2 to 3. Preferably, the acid solubilizing step (b) is conducted for as time ranging from 15 min to 14 days, or more preferably, for a time ranging from 7h to 48h.

BRIEF DESCRIPTION OF THE DRAWINGS

FIG. 1 is generated from Example 3.

FIG. 2 is generated from Example 3.

FIG. 3 is generated from Table XXVII in Example 7.

FIG. 5 is generated from Table XXI in Example 4.

DETAILED DESCRIPTION

Figure 1:
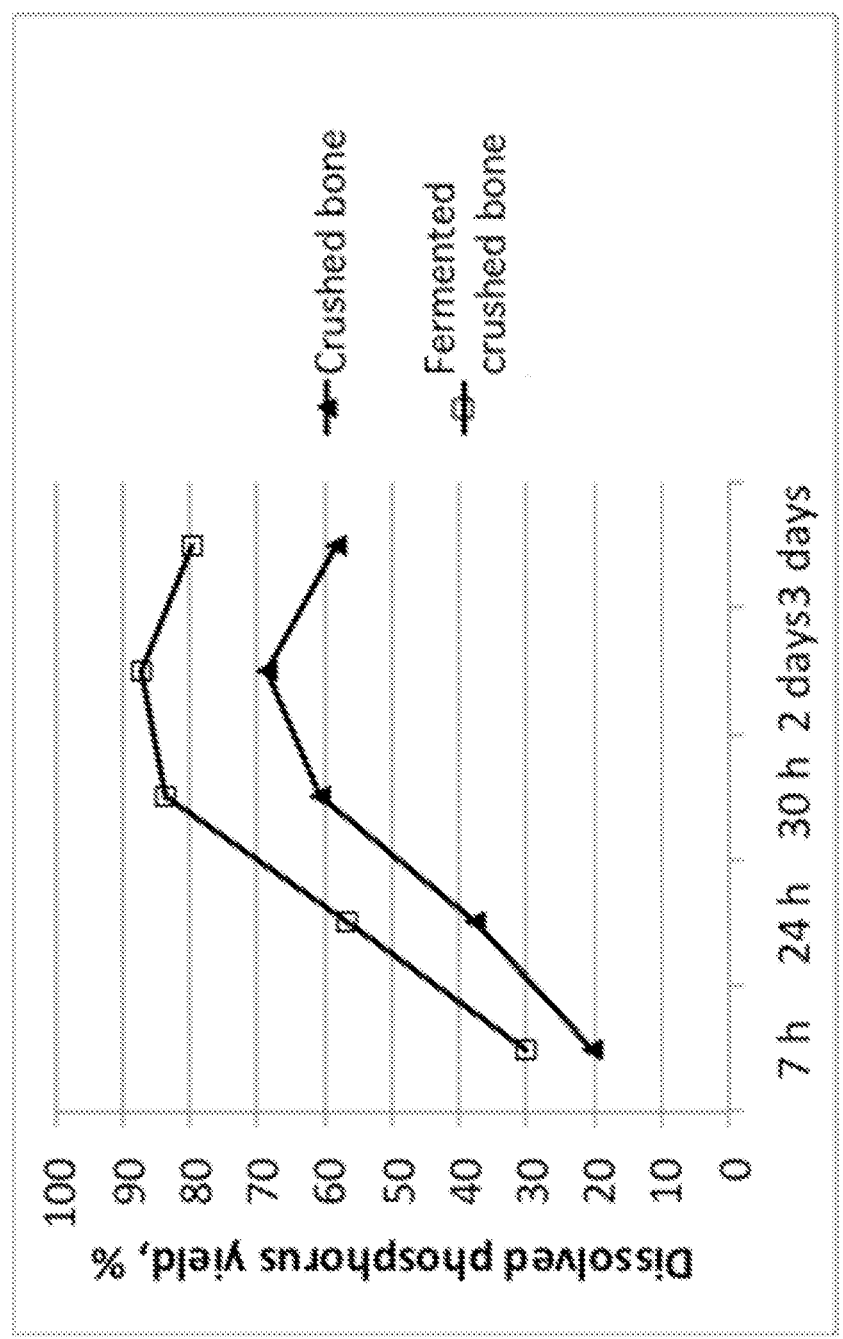
FIG. 1 illustrates the results of experiments to determine the effects of the fermentation of crushed bone on the phosphorous compounds solubilized from crushed bone by citric acid. The amount of citric acid was 117 g per 1 kg crushed bone. The results are the averages of three parallel experiments. The yield of the dissolved phosphorus was determined as a mass percent of the phosphorus content of the crushed bone.

Accordingly, the present invention provides improved methods for the solubilization and extraction of phosphorous compounds, such as phosphates, from animal by-products, farm and food processing wastes. Typically, slaughterhouse waste, for example, bovine and porcine by-products, contain a high proportion of organic matter (e.g., connective tissue muscle, blood and fat) and a minor proportion of bones. The organic matter needs to be removed in order to facilitate solubilization of phosphates from the bone fraction by means of acid solubilization.

The two-step process according to present invention starts with a fermentation step and thereafter continues with a post-fermenting step of adding acid to the product of the fermentation step. The acid lowers the pH and solubilizes phosphates. The fermentation step is conducted in order to remove and or break up the organic material, thus facilitating the acid solubilization step. For example, the organic material present in bone containing material is primarily a protein matrix that interferes with the acid solubilization step hy reacting with the acid and producing potentially explosive compounds. In addition, removal of the organic material from the bone itself reduces the amount of acid needed for the acid solubilization step. The fermentation process is also optionally utilized to produce or co-produce ammonia for commercial applications or production of biofertilizers.

In order to more clearly appreciate the invention, the following terms are defined. The terms listed below, unless otherwise indicated, will be used and are intended to be defined as indicated. Definitions for other terms can occur throughout the specification. It is intended that all singular terms also encompass the plural, active tense and past tense forms of a term, unless otherwise indicated The term "phosphorus" refers to the chemical element phosphorus.

The term "phosphorous" is an adjective meaning containing phosphorus. It refers to phosphorous compounds, such as phosphates, e.g., calcium phosphates, suitable for use as fertilizer or conversion to other useful compounds.

The term "MBM" or "meat-and-bone meal" as employed herein is defined by European Union Commission Regulation No. 142/2011 "meat-and-bone meal means animal protein derived from the processing of Category 1 or Category 2 materials in accordance with one of the processing methods set out in Chapter III of Annex IV" of European Union Commission Regulation No. 142/2011, incorporated by reference herein in its entirety.

In order to induce the mixed bacterial populations preferably employed in the fermentation stage of the inventive process, MBMs (designated infra as MBM1 and MBM2, respectively, were produced from animal by-products according to methods described in EU Commission Regulation 142/2011, and consisted of category 3 (EC Regulation 1069/2009) low infection risk material. In particular, MBM1 was obtained from Findest Protein Oy, Finland, and MBM2 was obtained from SARIA Bio-Industries AG & Co. KG, Germany.

The term, "crushed bone" refers to bone waste from agriculture, food processing, restaurants and the like, that has been prepared by crushing.

The terms "fermentation" or "fermenting" refer to a process where organic molecules serve as both electron donors and acceptors. It differs from respiration, where electrons derived from nutrient molecules are donated to oxygen (aerobic respiration) or other inorganic molecules/ions such as nitrate, sulfate, carbon dioxide or ferric iron (anaerobic respiration). In fermentation, nutrient molecules are reduced to small organic molecules such as volatile fatty acids and alcohols.

The term "ammonification" refers to the mineralization of nitrogen in organic macromolecules, conversion of organic nitrogen to ammonium or ammonia, is called ammonification. It is performed by ammonifying bacteria and consists of enzymatic hydrolysis of proteins to amino acids, and release of nitrogen as ammonium/ammonia through deamination and elimination reactions. Carbon backbones of amino acids are fermented to organic acids The term "ammonia" refers to the compound $NH_3$ found in gaseous form or dissolved in a non-ionized form in a medium e.g., an aqueous medium. The term "ammonium" refers to the ion $NH_4^+$ which is the ionic form of $NH_3$ found in e.g., aqueous solution. In aqueous solution, ammonium and ammonia occur in an equilibrium that is dependent on temperature and pH, e.g. the higher the temperature and the pH, the greater the proportion that is in the form of ammonia. For this reason, reference to "ammonia" herein with regard to the inventive process and/or ammonification microorganisms and products thereof should be understood to include reference to both $NH_3$ and $NH_4^+$ forms of this compound, unless otherwise indicated. For example, discussion of ammonification microorganisms as "ammonia producing" or "ammonium producing" is understood to include production of $NH_3$ and/or $NH_4^+$ according to the $NH_3/NH_4^+$ equilibrium found in the particular medium.

The inventive process provides methods for producing or recovering phosphorous compounds, e.g., phosphates, from an organic material. Broadly, the method includes, but is not limited to, two steps, which may be conducted separately and/or in combination. The method includes, e.g.,
  (a) fermenting an organic material in a medium in the presence of at least one microorganism, wherein the fermenting is under conditions, and for a sufficient period of time, to produce a fermentation product;
  (b) treating the solid fermentation product with acid to solubilize phosphates from the fermentation product;
wherein the organic material, and thus the solid fermentation product, comprises bone suitable for extraction of phosphates.

While not wishing to be limited to any theory or hypothesis as to the operation of the invention, it is believed that the fermentation process removes the bulk of the non-mineral component from the organic material. For example, when the organic material is MBM or crushed bone, it is believed that the fermentation process removes the bulk of muscle and/or connective tissue proteins, thus increasing the exposure of the residual bone mineral to dissolution and/or solubilization by contact with aqueous media having an acid pH.

The fermentation process can be conducted with any suitable microbial organisms, under anaerobic or aerobic conditions in a suitable reaction chamber or vessel for a time period and in a temperature range effective for efficient reduction of the organic material. The fermentation process is optionally conducted with at least one microorganism that is capable of ammonification. The advantage of fermenting the organic material with an ammonification microorganism is that ammonia or ammonium can be co-produced, while the instant invention provides for producing and/or recovering phosphorous compounds from a mineral component of the processed organic material.

The fermentation process is generally conducted with an organic material ranging in density from 10 to 50, g/100 ml (wt/vol) of aqueous medium. Preferably, fermentation process is conducted with an organic material ranging in density from 20 to 40, g/100 ml(wt/vol) of aqueous medium.

The fermentation process is generally conducted with an inoculum of fermentation microorganisms ranging in dose from 1 to 20 (vol-%) determined. Preferably, the fermentation process is conducted with an inoculum of fermentation microorganisms ranging in density from 5 to 10 (vol-%).

The fermentation step of the process is generally conducted at a temperature ranging from 30 to 60° C. Preferably, the process is conducted at a temperature ranging from 40 to 55° C. of aqueous medium.

The fermentation step of the process is generally conducted for a time ranging from 1 to 7 days. Preferably, the process is conducted for a time ranging from 2 to 3 days.

Processes and microorganisms for efficiently producing ammonia or ammonium by fermenting organic material, such as MBM, are disclosed, for instance, by co-owned U.S. Patent Appl. Ser. No. 13/722,228, filed on Dec. 20, 2012, claiming the benefit of U.S. Provisional Appl. Ser. No. 61/659,647, filed on Jun. 14, 2012, and by co-owned U.S. Patent Appl. Ser. No. 14/066,089, filed on Oct. 29, 2013, the contents of both of which are incorporated by reference herein in their entireties.

Exemplary single-strain bacteria for fermenting organic material according to the present invention and producing ammonia include, for example, strains taught by co-owned U.S. patent application Ser. No. 13/722,228. These include, for example, "Strain 385" that belongs to the *Clostridium genus, beijerinckii* or *butyricum species,* and that is deposited as VII E-123273 (VTT collection of Industrial Microorganisms, Finland) and "Strain 393" that belongs to *Clostridium genus, perfringens species,* and is deposited as VII E-123272 (VTT collection of Industrial Microorganisms, Finland) under the terms of the Budapest Treaty, in support of co-owned U.S. patent application Ser. No. 13/722,228.

Exemplary populations of bacteria for fermenting organic material according to the present invention and producing ammonia include, for example, defined mixed bacterial populations S1, FI1 and FO2 as detailed hereinbelow and produced by methods described in the above-noted co-owned U.S. patent application Ser. No. 14/066,089, filed on Oct. 29, 2013. In brief, mixed bacterial populations designated as S1, FI1 and FO2 were obtained as follows.

The S1 mixed bacterial population was created by mixing non-sterile MBM2 with cold tap water in a proportion of 180 g MBM per liter of water. MBM2 was cultured without aeration at 50° C. until $NH_3$ concentration leveled out, and stationary growth phase was reached as explained hereinbelow.

The S1 population has been deposited as a patent deposit, under the terms of the Budapest treaty, in support of co-owned U.S. Application Ser. No. 14/066,089 (as above), in the Centraalbureau voor Schimmelcultures (CBS), located at Uppsalalaan 8 3584 CT Utrecht, The Netherlands, as (CBS Accession No. 136063) on Aug. 22, 2013.

The FI1 population was created by mixing non-sterile field (FI) soil with cold tap water in as proportion of 180 g soil per liter of water. The mixture was cultured without aeration at 50° C.

The FO2 population was created by mixing non-sterile forest (FO) soil with boiling tap water in a proportion of 180 g of soil per liter at water. The mixture was let cool to room temperature. Both mixtures were incubated without aeration at 50° C. After 7 days incubation, 5 ml of each culture was inoculated in 100 ml of sterile MBM1 medium [180 g meat-and-bone meal 1 (MBM1) per liter of water]. The cultures were incubated at 50° C. for 7 days.

Growth of the mixed bacterial populations was monitored by measuring the ammonium production of the populations. A maximal ammonia level of about 8-10 g/l was repeatedly determined for culture growth under the conditions described above. Therefore, when the ammonia concentration reached this level, it was interpreted, as transition to stationary phase of growth. The diverse nature of the populations restricted the use of culture based methods for cell counting, and opacity of the MBM medium prevented the use of optical density measurement for estimation of cell densities. In all the following, "inocula of mixed bacterial populations" refer to bacterial cultures, which have reached stationary growth phase.

All populations were maintained by storing the liquid culture at +4° C.

As noted in co-owned U.S. application Ser. No. 14/066,089 (as above), the optimal temperature range for ammonification (via fermentation) by S1 mixed bacterial population is 37-60° C. However, S1 retained some of its ammonification efficiency even at room temperature (RT, 23° C.) and 70° C. In addition, the optimal pH range for ammonification (via fermentation) by S1 is about pH 6 to about pH 9.

Thus, the working range for ammonification by fermentation of proteinacious materials with S1 mixed bacterial population is as follows: Temperatures from 23° C. to 7° C., more particularly from 37-60° C., and pH 6-9 were the best for bacterial ammonification with S1 population described here. Ammonification by fermentation works in anaerobic, microaerobic, and aerobic conditions using the mixed S1 bacterial population.

Additional mixed bacterial populations are also disclosed by co-owned U.S. application Ser. No. 14/066,089 (as above), and are contemplated to be employed in the inventive process of the present invention. These additional mixed bacterial populations were obtained from MBM2 (A1, C1, H1, and P1), broiler chicken by-product (CBP-M), porcine/bovine by-product (PB-M), chicken feather (FE-M), fish by-product (MF-M), crushed porcine/bovine bone (CB-M), field soil mixed with boiling water (FI2) and forest soil mixed with cold water (FO1).

In certain embodiments, the process of the invention can e conducted wherein the fermentation step is conducted at a different location and the fermentation product is acid treated at a later time.

The process of the invention is contemplated to be conducted by extracting phosphorous compounds from the fermentation product with any suitable inorganic or organic acid. Simply by way of example, suitable acids include, e.g. citric acid, glutaric acid, maleic acid, malic acid, malonic acid, oxalic acid, tartaric acid, acetic acid, formic acid, hydrochloric acid, lactic acid, sulfuric acid, mixtures thereof, e.g., mixtures of acetic and citric acids. Preferably, the acid is an organic acid such as tartaric acid, malic acid and/or citric acid. Alternatively the acid is an inorganic acid, such as hydrochloric acid or sulfuric acid. Of the later, sulfuric acid is preferred.

The acid solubilization step of the process is generally conducted at a pH ranging from 1 to 6. Preferably, the process is conducted at a pH ranging from 2 to 3 and for a time ranging from 15 min to 14 days, or more preferably for a time ranging from 7 h to 48 h.

EXAMPLE 1

Acid Solubilization of Phosphorus Compounds from Meat Bone Meal (MBM)

Different acids, including organic and inorganic acids, were tested to determine which acids are the most effective in solubilizing phosphorus compounds from meat bone meal (MBM). The tested acids were boric acid (manufacturer VWR LLC, Belgium), citric acid (YA pharmacy, Finland), maleic acid (Sigma-Aldrich, Austria), DL-malic acid (Sigma-Aldrich, Germany), malonic acid (Sigma-Aldrich, Chine), oxalic acid (Sigma-Aldrich, USA), tannic acid (Sigma-Aldrich, Belgium), L-(+)-tartaric acid (Sigma-Aldrich, Italy), tartaric acid (YA pharmacy, Finland), acetic acid (Sigma-Aldrich, Germany), formic acid 98% (VWR LLC or Sigma-Aldrich, Germany). Organic acids were interesting because they have a biological origin, whereas inorganic acids are derived from mineral sources. In addition, some of the organic acids can be produced biotechnically which makes them a more environmentally sustainable option. Nitric acid was excluded from the experiments due to its higher price compared to another inorganic acid, sulfuric acid. The bone feedstocks were meat bone meal (MBM).

Tested Acids

The experiment was conducted to test the properties of different acids to solubilize phosphorus compounds from MBM at room temperature (RT). The phosphorus content of the MBM employed in the experiments was 6.2%, and the moisture content was 3.4%. The acids tested in the experiments are presented in Table I. Some of the acids were purchased as solid crystallized powders and some of them were purchased as liquids. The acids were chosen based on their $pK_a$ values and solubilities in water. The $pK_a$ value reflects how strongly the acid retains a proton or how widely the acid is protolyzed in water. If the pH of a water solution is the same as the $pK_a$ value of the acid, then 50% of the acid is in the anionic form and 50 is in the undissociated form. Most of the tested acids had small $pK_a$ values (high acidities) and good solubilities in water. In addition, some weaker and less soluble acids were tested to determine the differences between the solubilizing properties of the different acids.

TABLE I

The tested acids in the initial experiments and their $pK_a$ values and water-solubilities. Water-solubilities of the acids that are liquid at room temperature are not presented

| Acid | $pK_a$-values | Solubility in water, g/l (20° C.) |
|---|---|---|
| Boric acid | 9.23 | 40-50 |
| Citric acid | 3.13, 4.77, 6.39 | 750 |
| Glutaric acid | 4.31, 5.41 | 430 |
| Maleic acid | 1.83, 6.07 | 790 (25° C.) |
| DL-Malic acid | 3.4, 5.11 | 558 |
| Malonic acid | 2.83 | 1400 |
| Oxalic acid | 1.23, 4.19 | 90 |

TABLE I-continued

The tested acids in the initial experiments and their $pK_a$ values and water-solubilities. Water-solubilities of the acids that are liquid at room temperature are not presented

| Acid | $pK_a$-values | Solubility in water, g/l (20° C.) |
|---|---|---|
| Tannic acid | circa 10 | 250 |
| L-(+)-Tartaric acid | 2.98, 4.34 | 1390 |
| Acetic acid | 4.76 | miscible |
| Formic acid | 3.75 | miscible |
| Hydrochloric acid | −8 | miscible |
| L-(+)-Lactic acid | 3.08 | miscible |
| Sulfuric acid | −3 | miscible |
| Mixture or acetic and citric acids | — | miscible |

Initial Experiments were Conducted on a Test Tube Scale

The first part of the initial determination of phosphorus solubility was conducted on a test tube scale and by using MBM medium, which was made by adding 1 liter of RO (reverse osmosis) water to 180 g meat bone meal. The concentration of MBM in this medium was 161 g/l. First, the MBM medium and the acid solution were mixed according to Table II. The mixture was shaken to properly mix the MBM and the acid. Then the mixture stayed at room temperature without any mixing. As the acid treatment continued, timed 1 ml samples were taken and centrifuged at 20,000×g (Eppendorf) for three minutes. The separated liquid, supernatant, was collected and was diluted with water with a dilution ratio of 1:20 (50 μl (microliter) supernatant+950 μl milli-Q water (water purified using a Millipore Milli-Q lab water system)) to stop the reaction between the acid and MBM. The diluted supernatant was used for determination of dissolved phosphates. The phosphates were measured spectrophotometrically (Synergy HI Reader) using a Malachite green phosphate assay kit (POMG-25H, BioAssay Systems) according to the manufacturer's instructions. The results are presented in Table III.

TABLE II

The initial experiments performed in a test tube scale. Meat bone meal (MBM) medium contained 161 g/l meat bone meal. First the acid solution was made in milli-Q water after which it was added to MBM medium.

| Number of experiment | Volume of MBM medium, ml | Acid solution | Volume of acid solution, ml | Time of acid treatment, h |
|---|---|---|---|---|
| 1 | 4 | 50 g/l Boric acid | 0.2 | 20 |
| 2 | | | 2 | |
| 3 | 4 | 480 g/l Citric acid | 0.2 | 20 |
| 4 | | | 0.4 | |
| 5 | | | 0.6 | |
| 6 | | | 0.8 | |
| 7 | | | 1 | |
| 8 | | | 2 | |
| 9 | 4 | 90 g/l Oxalic acid | 0.5 | 24 |
| 10 | 3 | | 1.5 | |
| 11 | 2 | | 2.5 | |
| 12 | 2 | | 4 | |
| 13 | 4 | 125 g/l Tannic acid | 0.2 | 20 |
| 14 | | | 2 | |
| 15 | 4 | 50% Acetic acid | 0.2 | 20 |
| 16 | | | 0.4 | |
| 17 | | | 0.6 | |
| 18 | | | 0.8 | |
| 19 | | | 1 | |

TABLE II-continued

The initial experiments performed in a test tube scale. Meat bone meal (MBM) medium contained 161 g/l meat bone meal. First the acid solution was made in milli-Q water after which it was added to MBM medium.

| Number of experiment | Volume of MBM medium, ml | Acid solution | Volume of acid solution, ml | Time of acid treatment, h |
|---|---|---|---|---|
| 20 | 4 | 98% Formic acid | 0.215 | 24 |
| 21 |   |   | 1.026 |   |
| 22 | 4 | 37% Hydrochloric acid | 0.4 | 20 |
| 23 |   |   | 0.6 |   |
| 24 |   |   | 0.8 |   |
| 25 | 4 | 85% L-(+)-Lactic acid | 0.25 | 24 |
| 26 |   |   | 1.231 |   |
| 27 | 4 | 95% Sulfuric acid (VWR) | 0.2 | 20 |
| 28 |   |   | 0.4 |   |
| 29 | 4 | 48% Acetic acid + 48% citric acid | 0.1 + 0.1 | 20 |
| 30 |   |   | 0.2 + 0.2 |   |
| 31 |   |   | 0.3 + 0.3 |   |
| 32 |   |   | 0.4 + 0.4 |   |
| 33 |   |   | 0.5 + 0.5 |   |

TABLE III

The results of the initial experiments performed in a test tube scale. The amount of the used acid is presented as a mass per 1 kg MBM. The amoung of the dissolved phosphorus is presented as concentrations of dissolved phosphates and dissolved phosphorus and also as a yield of dissolved phosphorus from total phosphorus content of MBM.

| Number of experiment | Acid | Amount of acid per 1 kg MBM, g | Time of acid treatment, h | Concentration of dissolved phosphate, g/l | Yield of dissolved phosphorus, % |
|---|---|---|---|---|---|
| 1 | Boric acid | 16 | 20 | 0.17 | 0.5 |
| 2 |   | 155 |   | 0.13 | 0.6 |
| 3 | Citric acid | 149 | 20 | 6.61 | 20.4 |
| 4 |   | 298 |   | 10.00 | 32.5 |
| 5 |   | 447 |   | 13.85 | 47.3 |
| 6 |   | 596 |   | 15.72 | 56.2 |
| 7 |   | 745 |   | 15.13 | 56.6 |
| 8 |   | 1491 |   | 15.72 | 71.6 |
| 9 | Oxalic acid | 70 | 24 | 8.29 | 27.6 |
| 10 |   | 280 |   | 10.25 | 46.7 |
| 11 |   | 699 |   | 7.16 | 50.1 |
| 12 |   | 1118 |   | 6.10 | 57.7 |
| 13 | Tannic acid | 39 | 20 | 0.22 | 0.7 |
| 14 |   | 388 |   | 0.30 | 1.4 |
| 15 | Acetic acid | 266 | 20 | 2.61 | 8.1 |
| 16 |   | 532 |   | 4.02 | 13.1 |
| 17 |   | 798 |   | 4.61 | 15.7 |
| 18 |   | 1063 |   | 4.94 | 17.7 |
| 19 |   | 1329 |   | 5.16 | 19.3 |
| 20 | Formic acid | 399 | 24 | 10.81 | 33.5 |
| 21 |   | 1905 |   | 15.32 | 57.6 |
| 22 | Hydrochloric acid | 271 | 20 | 16.55 | 53.8 |
| 23 |   | 406 |   | 17.79 | 60.7 |
| 24 |   | 541 |   | 18.06 | 64.6 |
| 25 | L-(+)-Lactic acid | 398 | 24 | 12.65 | 39.5 |
| 26 |   | 1959 |   | 11.46 | 45 |
| 27 | Sulfuric acid | 542 | 20 | 15.65 | 48.3 |
| 28 |   | 1084 |   | 15.57 | 50.6 |
| 29 | Acetic acid + citric acid | 80 + 75 | 20 | 3.64 | 11.2 |
| 30 |   | 160 + 149 |   | 5.44 | 17.7 |
| 31 |   | 239 + 224 |   | 6.63 | 22.6 |
| 32 |   | 319 + 298 |   | 6.63 | 23.7 |
| 33 |   | 399 + 373 |   | 7.09 | 26.5 |

Initial Experiments in a Bottle Scale

The second part of the initial experiments for phosphorus solubilization was done in a bottle scale and by using MBM as a feedstock. First the acid solution was made and then added to the weighed MBM according to Tables IV and V. The experiments were conducted according to the same procedure as the experiments in a test tube scale. The results are presented in Tables VI and VII.

TABLE IV

The initial experiments performed in a bottle scale with the solic acids. First the acid was weighed in a measuring bottle which was then filled with milli-Q water until the total volume given was reached. After making the acid solution it was added to MBM. The samples from the bottles were taken after acid treatments of 24 h and 1 week.

| Number of experiment | Mass of MGM, g | Acid | Amount of acid, g | Total volume of acid solution, ml |
|---|---|---|---|---|
| 1 | 36 | Citric acid | 10 | 200 |
| 2 | 9 |   | 10 | 50 |

TABLE IV-continued

The initial experiments performed in a bottle scale with the solic acids. First the acid was weighed in a measuring bottle which was then filled with milli-Q water until the total volume given was reached. After making the acid solution it was added to MBM. The samples from the bottles were taken after acid treatments of 24 h and 1 week.

| Number of experiment | Mass of MGM, g | Acid | Amount of acid, g | Total volume of acid solution, ml |
|---|---|---|---|---|
| 3 | 7.2 | Glutaric acid | 2 | 40 |
| 4 | 7.2 | | 8 | 40 |
| 5 | 36 | Maleic acid | 10 | 200 |
| 6 | 9 | | 10 | 50 |
| 7 | 36 | DL-Malic acid | 10 | 200 |
| 8 | 9 | | 10 | 50 |
| 9 | 36 | Malonic acid | 10 | 200 |
| 10 | 9 | | 10 | 50 |
| 11 | 36 | Oxalic acid | 10 | 200 |
| 12 | 9 | | 4 | 50 |
| 13 | 36 | L-(+)-Tartaric acid | 10 | 200 |
| 14 | 9 | | 10 | 50 |

TABLE V

The initial experiments performed in a bottle scale with liquid acids. After making the acid solution in milli-Q water it was added to MBM. The samples from the bottles were taken after acid treatments of 24 h and 1 week.

| Number of experiment | Mass of MBM, g | Acid | Volume of acid, ml | Volume of water, ml | Total Volume of acid solution, ml |
|---|---|---|---|---|---|
| 15 | 36 | 80% Acetic acid | 12.500 | 187.500 | 200 |
| 16 | | | 50.000 | 150.000 | |
| 17 | 36 | 98% Formic acid | 10.204 | 189.796 | 200 |
| 18 | | | 40.816 | 159.184 | |
| 19 | 36 | 85% L-(+)-Lactic acid | 11.765 | 188.235 | 200 |
| 20 | | | 47.059 | 15.941 | |

TABLE VI

The results of the initial experiments performed in a bottle scale after acid treatment of 24 h. The amount of the used acid is presented as a mass per 1 kg MBM. The amount of the dissolved phosphorus is presented as concentrations of dissolved phosphates and dissolved phosphorus and also as a yield of dissolved phosphorus from phosphorus content of MBM.

| Number of experiment | Acid | Amount of acid per 1 kg MBM, g | Concentration of dissolved phosphate, g/l | Yield of dissolved phosphorus, % |
|---|---|---|---|---|
| 1 | Citric acid | 278 | 15.84 | 46.3 |
| 2 | | 1111 | 25.02 | 73.1 |
| 3 | Gluataric acid | 278 | 4.67 | 13.6 |
| 4 | | 1111 | 9.34 | 27.3 |
| 5 | Maleic acid | 278 | 11.24 | 32.8 |
| 6 | | 1111 | 29.87 | 87.3 |
| 7 | DL-Malic acid | 278 | 12.36 | 36.1 |
| 8 | | 1111 | 16.52 | 48.3 |
| 9 | Malonic acid | 278 | 14.52 | 42.4 |
| 10 | | 1111 | — | — |
| 11 | Oxalic acid | 278 | 26.78 | 78.2 |
| 12 | | 444 | 31.25 | 91.3 |
| 13 | L-(+)-Tartaric acid | 278 | 22.97 | 67.1 |
| 14 | | 1111 | 32.44 | 94.8 |
| 15 | Acetic acid | 297 | 5.17 | 15.1 |
| 16 | | 1189 | 8.26 | 24.1 |
| 17 | Formic acid | 339 | 16.11 | 47.1 |
| 18 | | 1356 | 26.97 | 78.8 |
| 19 | L-(+)-Lactic acid | 335 | 12.41 | 36.3 |
| 20 | | 1340 | 26.11 | 76.3 |

TABLE VII

The results of the initial experiments performed in a bottle scale after acid treatment of 1 week. The amount of the used acid is presented as a mass per 1 kg meat bone meal (MBM). The amount of the dissolved phosphorus is presented as concentrations of dissolved phosphates and dissolved phosphorus and also as a yield of dissolved phosphorus from phosphorus content of MBM.

| Number of experiment | Acid | Amount of acid per 1 kg MBM, g | Concentration of dissolved phosphate, g/l | Yield of dissolved phosphorus, % |
|---|---|---|---|---|
| 1 | Citric acid | 278 | 19.07 | 55.7 |
| 2 | | 1111 | 24.99 | 73.0 |
| 3 | Glutaric acid | 278 | 4.81 | 14.5 |
| 4 | | 1111 | 7.98 | 24.0 |
| 5 | Maleic acid | 278 | 9.70 | 28.4 |
| 6 | | 1111 | 23.38 | 68.3 |
| 7 | DL-Malic acid | 278 | 16.13 | 47.1 |
| 8 | | 1111 | 24.20 | 70.7 |
| 9 | Malonic acid | 278 | 12.67 | 37.0 |
| 10 | | 1111 | 24.01 | 70.2 |
| 11 | Oxalic acid | 278 | 23.63 | 69.1 |
| 12 | | 444 | 26.15 | 76.4 |
| 13 | L-(+)-Tartaric acid | 278 | 19.09 | 55.8 |
| 14 | | 1111 | 27.19 | 79.5 |
| 15 | Acetic acid | 297 | 3.43 | 10.0 |
| 16 | | 1189 | 8.60 | 25.1 |
| 17 | Formic acid | 339 | 13.36 | 39.0 |
| 18 | | 1356 | 24.17 | 70.6 |
| 19 | L-(+)-Lactic acid | 335 | 10.52 | 30.8 |
| 20 | | 1340 | 21.36 | 62.4 |

Boric acid, tannic acid and acetic acid were found to be the weakest acid to dissolve phosphorus from bone.

EXAMPLE 2

Comparing Acids for Solubilizing Phosphorus Compounds from Crushed Bone

The acids were selected based on the results of Example 1. In practice the least efficient acids in solubilizing phosphorus compounds from MBM were excluded from the later experiments based on the initial experiments. Hydrochloric acid also was excluded due to its higher price compared to another inorganic acid, sulfuric acid. The bone feedstock that was employed was crushed bone (a/k/a "bone crush," or "BC," manufactured by Oy Musch Ltd., Pietarsaari, Finland), which contained bovine and pork bones. The crushed bone composition that was tested is presented in Table VIII.

TABLE VIII

Composition of the used crushed bone matrix (analysed by Novalab, Karkkila, Finland).

| | |
|---|---|
| Phosphorus, % | 2.2-2.7 |
| Nitrogen, % | 2.6-2.9 |
| Organic matter in dry matter, % | 68 |
| Moisture, % | 53.8-60.7 |

The crushed bone used in these experiments contained 67% organic matter and 33% of inorganic matter/material in dry matter. The total amount or phosphorus was 2.7% of the material (crushed bone). The bone material contained 28.9% nitrogen and 53.8% moisture. The solid acids were citric acid, maleic acid, DL-malic acid, malonic acid, oxalic acid, L-(+)-tartaric acid and tartaric acid (purchased from pharmacy). The acid solutions from the solid acids were made as presented in Tables IX and X. The liquid acids were formic acid, L-(+)-lactic acid and sulfuric acid (VWR). The acid solutions from the liquid acids were made as presented in Table XI. The concentrations of the acid solutions were determined based on their mass percent in the reaction mixture consisting of crushed bone and acid solution. 80 g crushed bone was weighed in glass bottles and each of the made 200 ml acid solutions was added to one bottle. Though the moisture content of the crushed bone was high, 53.8-60.7%, it was observed that the volume of the added acid solution was not changed due to the moisture of the bone feedstock. The experiments were conducted at room temperature according to the same procedure as the experiments in Example 1. The results are presented in Table XII.

TABLE IX

Making the acid solutions of the solid acids which were citric acid, oxalic acid, L-(+)-tartaric acid and tartaric acid (purchased from pharmacy). The total volume of each acid solution was 200 ml and the solutions were made in milli-Q water.

| Mass percent of acid in reaction mixture, % | Amount of acid, g | Concentration of acid solution, g/l |
|---|---|---|
| 2 | 5.6 | 28 |
| 5 | 14.0 | 70 |
| 7 | 19.6 | 98 |
| 10 | 28.0 | 140 |

TABLE X

Making the acid solutions of the solid acids which were maleic acid, DL-malic acid and malonic acid. The solutions were made in milli-Q water.

| Mass percent of acid in reaction mixture, % | Amount of acid, g | Concentration of acid solution, g/l | Volume of acid solution, ml |
|---|---|---|---|
| 1.7 | 5.6 | 22.4 | 250 |
| 4.2 | 14.0 | 56 | 250 |
| 5.9 | 19.6 | 78.4 | 250 |
| 8.5 | 28.0 | 112 | 250 |
| 10 | 28.0 | 140 | 200 |

TABLE XI

Making the acid solutions of the liquid acids in milli-Q water. The total volume of each acid solution was 200 ml. The density of 98% formic acid was 1.22 kg/l, the density of 85% L-(+)-lactic acid was 1.206 kg/l and the density of 95% sulfuric acid was 1.837 kg/l.

| Acid | Mass percent of acid in reaction mixture, % | Amount of 100% acid, g | Volume of used acid, ml | Volume of water, ml | Concentration of acid solution, g/l |
|---|---|---|---|---|---|
| 98% Formic acid | 2 | 5.6 | 4.7 | 195.3 | 28 |
| | 5 | 14.0 | 11.7 | 188.3 | 70 |
| | 7 | 19.6 | 16.4 | 183.6 | 98 |
| | 10 | 28.0 | 23.4 | 179.6 | 140 |
| 85% L-(+)-Lactic acid | 2 | 5.6 | 5.5 | 194.5 | 28 |
| | 5 | 14.0 | 13.7 | 186.3 | 70 |
| | 7 | 19.6 | 19.1 | 180.9 | 98 |
| | 10 | 28.0 | 27.3 | 172.7 | 140 |
| 95% Sulfuric acid | 2 | 5.6 | 3.2 | 196.8 | 28 |
| | 5 | 14.0 | 8.0 | 192.0 | 70 |
| | 7 | 19.6 | 11.2 | 188.8 | 98 |
| | 10 | 28.0 | 16.0 | 184.0 | 140 |

TABLE XII

The best results in different acid concentrations of the best acids in the solubilzation of phosphorus. The experiments were conducted at room temperature.

| Mass percent of acid in reaction mixture, % | Acid | Amount of acid per 1 kg of crushed bone, g | Time of acid treatment | Concentration of dissolved phosphate, g/l | Yield of dissolved phosphorus, % |
|---|---|---|---|---|---|
| 2 | Citric | 70 | 24 h | 9.10 | 27.5 |
| 5 | acid | 175 | 8 d | 22.8 | 68.7 |
| 7 | | 245 | 10 d | 26.1 | 78.7 |
| 10 | | 350 | 10 d | 23.9 | 72.2 |
| 2 | L-(+)- | 70 | 24 h | 9.4 | 28.3 |
| 5 | Tartaric | 175 | 7 d | 21.2 | 64.1 |
| 7 | acid | 245 | 8 d | 20.5 | 62.0 |
| 10 | | 350 | 10 d | 23.2 | 70.1 |
| 5 | Tartaric | 175 | 14 d | 20.3 | 61.2 |
| 7 | acid (from | 245 | 13 d | 25.5 | 75.9 |
| 10 | pharmacy) | 350 | 7 d | 21.4 | 64.5 |
| 2 | Oxalic | 70 | 24 h | 14.1 | 42.1 |
| 5 | acid | 175 | 8 d | 26.8 | 80.7 |
| 7 | | 245 | 8 d | 26.7 | 86.3 |
| 10 | | 350 | RT, 6 d | 29.0 | 86.0 |
| 1.7 | DL-malic | 70 | 24 h | 7.0 | 26.5 |
| 4.2 | acid | 175 | 24 h | 15.2 | 57.0 |
| 5.9 | | 245 | 10 d | 20.8 | 78.0 |
| 8.5 | | 350 | 14 d | 25.6 | 96.4 |
| 10 | | 350 | 8 d | 32.6 | 98.1 |
| 1.7 | Maleic | 70 | 3 h | 6.4 | 23.9 |
| 4.2 | acid | 175 | 3 d | 13.2 | 49.4 |
| 5.9 | | 245 | 6 d | 21.8 | 80.7 |
| 8.5 | | 350 | 3 d | 25.9 | 96.8 |
| 10 | | 350 | 14 d | 31.5 | 94.5 |
| 1.7 | Malonic | 70 | 3 h | 12.0 | 45.2 |
| 4.2 | acid | 175 | 24 h | 16.0 | 59.9 |
| 5.9 | | 245 | 13 d | 22.8 | 85.8 |
| 8.5 | | 350 | 13 d | 26.6 | 99.2 |
| 10 | | 350 | 8 d | 27.0 | 85.8 |
| 2 | L-(+)- | 70 | 5 h | 5.9 | 17.7 |
| 5 | Lactic | 175 | 24 h | 27.0 | 80.5 |
| 7 | acid | 245 | 7 d | 22.0 | 65.7 |
| 10 | | 350 | 3 d | 27.6 | 82.8 |
| 2 | Formic | 70 | 7 h | 12.0 | 35.9 |
| 5 | acid | 175 | 24 h | 23.0 | 69.1 |
| 7 | | 245 | 3 d | 22.7 | 80.8 |

TABLE XII-continued

The best results in different acid concentrations of the best acids in the solubilzation of phosphorus. The experiments were conducted at room temperature.

| Mass percent of acid in reaction mixture, % | Acid | Amount of acid per 1 kg of crushed bone, g | Time of acid treatment | Concentration of dissolved phosphate, g/l | Yield of dissolved phosphorus, % |
|---|---|---|---|---|---|
| 10 | | 350 | 8 d | 25.8 | 96.5 |
| 2 | Sulfuric | 70 | 7 h | 15.2 | 45.6 |
| 5 | acid | 175 | 7 d | 40.3 | 84.6 |
| 7 | | 245 | 7 d | 43.7 | 92.0 |
| 10 | | 350 | 6 d | 40.9 | 85.6 |

Conclusions on the Example 2: Based on experiments it appears that phosphorus can be dissolved from crushed bone if sufficient time is allowed for solubilization.

EXAMPLE 3

Positive Effect of Fermentation Step to Process of Solubilizing Phosphorus Compounds from Crushed Bone In this Example, crushed bone was first fermented and then subjected to solubilization using to selected set of acids.

The fermentation step was performed in the following manner: First the crushed bone was weighed in a bucket, then tap water was added to the crushed bone and stirred with a suitable spatula. The mixture was preheated to 50° C. in an incubator. Then a mixed population of bacterial inoculum, typically 5 vol-% (volume percent), capable of ammonification (S1 population as defined by Table XIII(a) below) was inoculated into the mixture.

TABLE XIII(a)

Bacterial diversity analysis results: genera and species in populations S1, FI1 and FO2. Cells from all cultures were harvested for DNA extraction at the age of four days i.e. 96 h after inoculating sterile MBMI medium with the population and incubating at 50° C. The results are expressed as percentage of total population.

| Species | S1 | FI1 | FO2 |
|---|---|---|---|
| Alicyclobacillus contaminans | | | 0.23 |
| Bacillus beijingensis | | | 0.02 |
| Bacillus benzoevorans | | | 0.02 |
| Bacillus coagulans | | | 8.71 |
| Bacillus ginsengi | | | 0.02 |
| Bacillus nealsanii | | | 0.06 |
| Bacillus pichinotyi | | | 0.02 |
| Bacillus smithii | | | 0.02 |
| Bacillus sp. | 0.40 | | 29.82 |
| Bacillus thermoamylovorans | 0.09 | | |
| Bacillus vireti | | | 0.04 |
| Caldicoprobacter oshimai | 0.09 | | |
| Caloramator sp. | 5.20 | 0.75 | |
| Carnobacterium divergens | | | 0.06 |
| Clostridium beijerinckii | | | 0.04 |
| Clostridium botulinum | 4.63 | | |
| Clostridium cachlearium | 8.50 | 1.80 | 0.06 |
| Clostridium oceanicum | 0.06 | | |
| Clostridium pasteurianum | | | 0.45 |
| Clostridium purinilyticum | | 0.03 | |
| Clostridium sp. | 0.57 | 6.34 | 16.16 |
| Clostridium sporogenes | 0.48 | 3.68 | 0.06 |
| Clostridium tyrobutyricum | | | 0.06 |
| Clostridium ultunense | 1.25 | 2.82 | |
| Clostridium xylanovorons | | | 0.08 |
| Empedobacter brevis | | | 0.02 |
| Enterobacter cloacoe | | | 0.02 |

TABLE XIII(a)-continued

Bacterial diversity analysis results: genera and species in populations S1, FI1 and FO2. Cells from all cultures were harvested for DNA extraction at the age of four days i.e. 96 h after inoculating sterile MBMI medium with the population and incubating at 50° C. The results are expressed as percentage of total population.

| Species | S1 | FI1 | FO2 |
|---|---|---|---|
| Enterococcus azikeevi | | | 0.04 |
| Enterococcus faecalis | | | 0.30 |
| Enterococcus faecium | | | 1.06 |
| Enterococcus hirae | | 0.05 | 0.04 |
| Enterococcus raffinosus | | | 0.02 |
| Enterococcus sp. | | | 0.02 |
| Faecalibacterium prausnitzil | | | 0.02 |
| Faecalibacterium sp. | | 0.03 | |
| Garciella sp. | 0.03 | | |
| Halobacillus trueperi | | | 0.04 |
| Klebsiella oxytoca | | | 0.04 |
| Lactobacillus pontis | | | 0.02 |
| Lactococcus garvieoe | | | 0.13 |
| Lactococcus raffinolactis | | | 0.06 |
| Lactococcus sp. | | | 0.13 |
| Mahella oustraliensis | 0.43 | 0.35 | |
| Pantoea sp. | | | 0.02 |
| Pediococcus acidilactici | | | 4.80 |
| Peptostreptococcus sp. | | 0.19 | |
| Petrobacter succinatimandens | | | 0.04 |
| Propionibacterium sp. | 0.03 | | |
| Pseudobutyrivibrio ruminis | 0.03 | | |
| Schlegelella thermodepolymerans | | | 0.13 |
| Shigella flexneri | | | 0.02 |
| Soehngenia sp. | | 0.03 | |
| Sporanaerobacter acetigenes | 75.87 | 77.63 | 0.04 |
| Sporolactobacillus inulinus | | | 0.08 |
| Streptococcus alactolyticus | | | 0.02 |
| Streptococcus mitis | | 0.03 | |
| Subdoligranulum variablile | | | 0.06 |
| Tepidanaerobacter sp. | 0.68 | 1.29 | |
| Thermoanaerobacterium aciditolerans | | | 0.89 |
| Thermoanaerobacterium aotearoense | | | 19.97 |
| Thermoanaerobacterium sp. | | | 0.28 |
| Thermoanaerobacterium thermosaccharolyticum | | | 15.65 |
| Tissierella sp. | 1.68 | 4.97 | 0.02 |
| Tuberibacillus calidus | | | 0.02 |

The fermentation broth contained 40% crushed bone, 55% water and 5% bacterial inoculum. It was in an incubator at temperature of 50° C. for three days. After a vacuum filtration step and washing with water the remained solid matter was the fermented crushed bone (FBC). Composition of the fermented crushed bone matrix is presented in Table XIII(b), below.

TABLE XIII(b)

Composition of the fermented crushed bone matric (analysed by Novalab, Karkkila, Finland). The fermented crushed bone was obtained after fermenting, vaccuum filtrating and water washing of crushed bone.

| | |
|---|---|
| Phosphorus, % | 6.8-6.9 |
| Nitrogen, % | 2.6-2.7 |
| Organic matter in dry matter, % | 34-39 |
| Moisture, % | 42.1-42.6 |

The crushed bone used in Example 3 contained 68% organic matter and 32% of inorganic matter/material, before fermentation. Total amount of phosphorus was 2.2%. of the material (crushed bone). The crushed bone material contained 25.9% nitrogen and 60.7% moisture.

Figure 2:
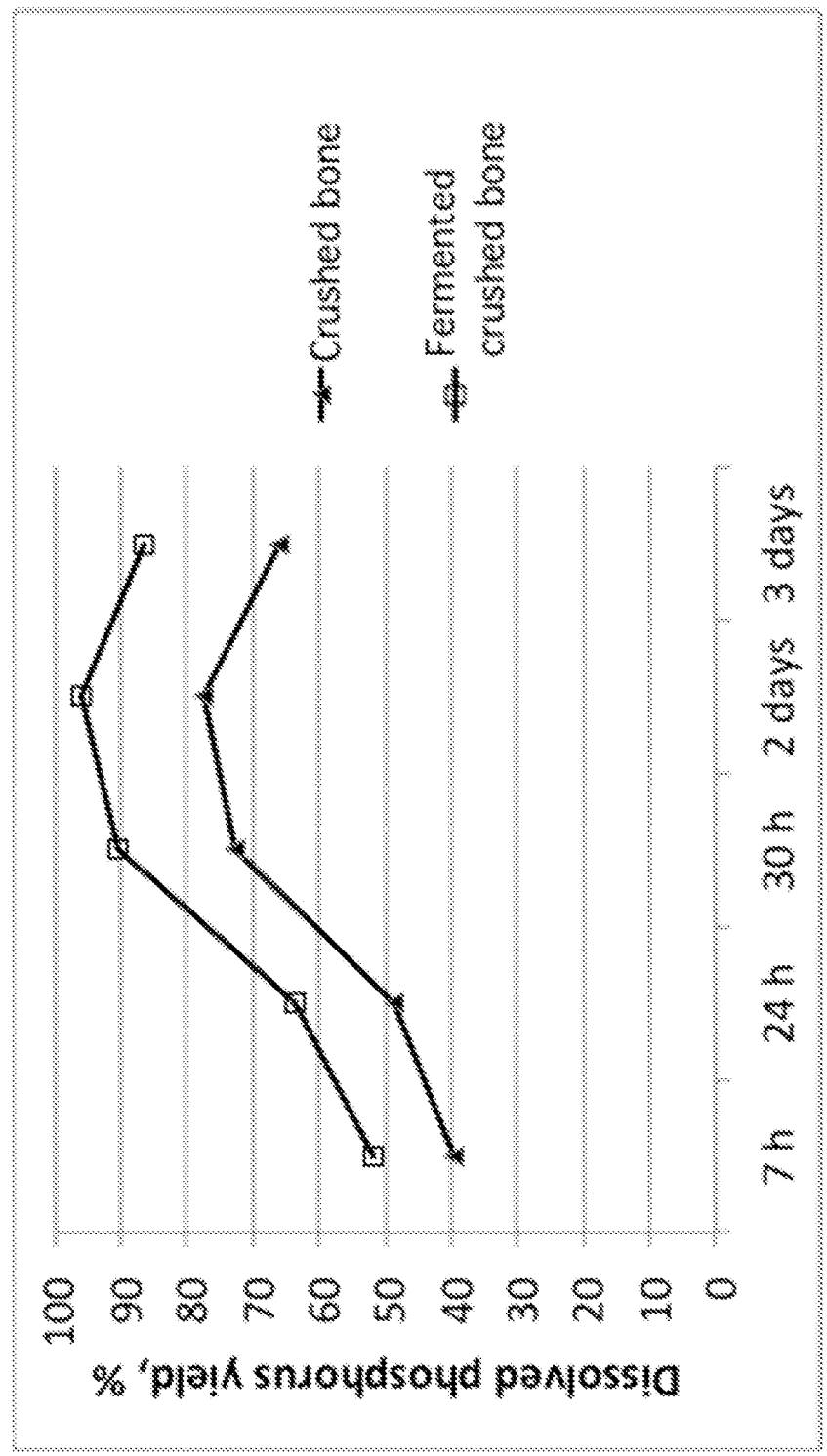
FIG. 2 illustrates the results of experiments to determine the effects of the fermentation of crushed bone on the phosphorous compounds solubilized from crushed bone by sulfuric acid. The amount of the acid was 117 g per 1 kg crushed bone. The results are the averages of three parallel experiments. The yield of the dissolved phosphorus was determined as a mass percent of the phosphorus content of the crushed bone.

120 g of crushed bone was weighed in six buckets, 165 ml of tap water was added to each bucket and mixed. 15 ml bacterial inoculum was added to each mixture and the suspension was mixed properly. The fermentation step was conducted as described earlier. As six 120 g crushed bone batches had been fermented, vacuum filtrated and washed 37.7-40.5% of the solid crushed bone remained. Each of six batches of the fermented crushed bone was mixed in a glass bottle with one of the acid solutions that were made according to Tables XII and XIII. 120 g crushed bone was weighed in six bottles and the acid solution was added to each bottle also according to Tables XIV and XV. Three parallel experiments were performed. The experiments were conducted at room temperature according to the same procedure as described in Example 1. The results are presented in Tables XVI and XVII and in FIGS. 1 and 2 respectively.

The ammonifying mixed bacterial populations include populations S1, FI1 and FO2 and variations thereon, and they are described hereinbelow in detail.

Bacterial community analysis of mixed populations S1, FI1 and FO2 was performed on DNA obtained by phenol-chloroform-isoamyl alcohol extraction from bacterial cultures where cells had been disrupted by bead beating. Populations had been cultured for four days at 50° C. in sterile MBM1 medium [180 g meat-and-bone meal 1 (MBM1) per liter of water]. Bacterial 16S gene assay by tag-encoded FLX amplicon pyrosequencing (bTEFAP) and bacterial diversity data analysis were performed by the Research and Testing Lab (Lubbock, Tex., USA) as described by Dowd et al. 2008a and Wolcott et al. 2009. Primers 28F 'GAGTTTGATCNTG-GCTCAG' (SEQ ID NO: 1) and 519R 'GTNTTACNGCG-GCKGCTG' (SEQ ID NO: 2) were used for amplification of 16S variable regions V1-3 (wherein "N" is A, T/U, G or C) and wherein K is T/U or G).

Bacterial diversity analysis revealed the presence of bacteria belonging to 33 different genera (TABLE XIII(a)). Of the total of 64 results, 50 were identified at the species level and 14 at the genus level. TABLE XIII(c), hereinbelow, presents the predominant bacterial genera and species in each population. Bacteria belonging to 6-7 genera form the majority of all populations. *Clostridium spp.* and *Sporanaerobacter acetigenes* are predominant in populations S1 and FI1. FO2 differs from S1 and FI1 in consisting predominantly of bacteria belonging to genera *Bacillus, Thermoanaerobacterium* and *Clostridium*.

TABLE XIII(c)

Predominant bacterial genera and species in populations S1, FI1 and FO2. The results are expressed as percentage of total population.

| Species | S1 | FI1 | FO2 |
|---|---|---|---|
| *Bacillus spp.* | 0.48 | 0 | 38.74 |
| *Caloramator spp.* | 5.20 | 0.75 | 0 |
| *Clostridium spp.* | 15.49 | 14.68 | 16.93 |
| *Enterococcus spp.* | 0 | 0.05 | 1.49 |
| *Pediococcus spp.* | 0 | 0 | 4.80 |
| *Sporanaerobacter acetigenes* | 75.87 | 77.63 | 0.04 |
| *Tepidanaerobacter sp.* | 0.68 | 1.29 | 0 |
| *Thermoanaerobacterium spp.* | 0 | 0 | 36.79 |
| *Tissierella spp.* | 1.68 | 4.97 | 0.02 |
| OTHER | 0.60 | 0.62 | 1.19 |
| TOTAL | 100 | 100 | 100 |

Correlation coefficients [TABLE XIII(d), hereinbelow] were calculated from data presented in TABLE XIII(a) using equation [1], where X and Y refer to two matrices, e.g. S1 and FI1, between which the correlation is calculated, x and y are single values within a matrix, and x and y are the means of all values within a matrix. Species not present in the population [empty cells in TABLE XIII(a)] were assigned a value 0.

$$Correl(X, Y) = \frac{\Sigma(x - \bar{x})(y - \bar{y})}{\sqrt{\Sigma(x - \bar{x})^2 \Sigma(y - \bar{y})^2}}$$ [Equation 1]

TABLE XIII(d)

Correlation coefficients between bacterial diversities of mixed populations calculated from data presented in TABLE XIII(a) using equation [1].

| | S1 | FI1 | FO2 |
|---|---|---|---|
| S1 | 1 | 0,9877 | −0,0416 |
| FI1 | 0,9877 | 1 | −0,0155 |
| FO2 | −0,0416 | −0,0155 | 1 |

The term "substantially similar" with respect to a bacterial population as disclosed herein, means that a bacterial population has a correlation coefficient of at least 0.8 when compared to one or more of the bacterial populations defined by TABLE XIII(a). Preferably, a substantially similar bacterial population has a correlation coefficient of at least 0.9, and more preferably, a substantially similar bacterial population has a correlation coefficient of at least 0.95 when compared to one or more of the bacterial populations defined by TABLE XIII(a). Other statistical methods for comparing populations can be used as well.

TABLE XIII(c) shows a very high similarity between all populations at the age of 4 days. The majority of all populations comprises of only a few species and genera, remaining very similar under all conditions tested and outcompeting innate populations present in animal-origin materials.

Bacterial diversity analyses based on sequencing molecular methods are biased due to e.g. primer specificity and universality (Dowd et al. 2008b). Therefore, the method described hereinabove must be used as a standard when comparisons to the mixed populations presented herein are performed.

TABLE XIV

The experiments performed with the crushed bone and the fermented crushed bone to test the influence of the fermentation on phosphorus solubilization using citric acid. The fermented crushed bone was obtained after fermenting, vaccum filtrating and washing of 120 g crushed bone. After making the acid solutions in milli-Q water each of the solutions was mixed with the crushed bone or the fermented crushed bone.

| Bone material | Acid solution | Amount of acid, g | Total volume of acid solution, ml | Amount of parallel experiments |
|---|---|---|---|---|
| 120 g crushed bone | Citric acid | 14 | 200 | 3 |
| Fermented crushed bone derived from 120 g crushed bone | Citric acid | 14 | 200 | 3 |

The experiments performed with the crushed bone and the fermented crushed bone to test the influence of the fermentation on phosphorus solubilization using sulfuric acid (Sigma-Aldrich). The fermented crushed bone was obtained after fermenting, vacuum filtrating and washing of 120 g crushed bone. After making the acid solutions in milli-Q water each of the solutions was mixed with the crushed bone or the fermented crushed bone.

| Bone material | Acid solution | Amount of 100% acid, g | Volume of acid solution, ml | Volume of water, ml | Amount of parallel experiments |
|---|---|---|---|---|---|
| 120 g crushed bone | 95% Sulfuric acid | 14 | 8.009 | 191.991 | 3 |
| Fermented crushed bone derived from 120 g crushed bone | 95% Sulfuric acid | 14 | 8.009 | 191.991 | 3 |

TABLE XVI

The results of the experiments to tet the influence of the fermentation on phosphorus solubilization using citric acid. The amount of the acid was 117 g per 1 kg crushed bone. Each result is the average of three parallel experiments. The yield of the solubilized phosphorus was determined as a mass percent of the phosphorus content of the crushed bone.

| | Crushed bone | | Fermented crushed bone | |
|---|---|---|---|---|
| Time of acid treatment | Concentration of dissolved phosphate, g/l | Yield of dissolved phosphorus, % | Concentration of dissolved phosphate, g/l | Yield of dissolved phosphorus, % |
| 7 h | 8.13 | 20.1 | 12.15 | 30.0 |
| 24 h | 15.29 | 37.8 | 22.95 | 56.7 |
| 30 h | 24.52 | 60.6 | 33.84 | 83.6 |
| 2 days | 27.82 | 68.7 | 35.36 | 87.4 |
| 3 days | 23.60 | 58.3 | 32.32 | 79.8 |

TABLE XVII

The results of the experiments to test the influence of the fermentation on phosphorus solubilization using sulfuric acid. The amount of the acid was 117 g per 1 kg crushed bone. Each result is the average of three parallel experiments. The yield of the dissolved phosphorus was determined as a mass percent of the phosphorus content of the crushed bone.

| | Crushed bone | | Fermented crushed bone | |
|---|---|---|---|---|
| Time of acid treatment | Concentration of dissolved phosphate, g/l | Yield of dissolved phosphorus, % | Concentration of dissolved phosphate, g/l | Yield of dissolved phosphorus, % |
| 7 h | 18.32 | 45.3 | 22.79 | 56.3 |
| 24 h | 15.95 | 39.4 | 20.89 | 51.6 |
| 30 h | 19.69 | 48.6 | 25.83 | 63.8 |
| 2 days | 29.46 | 72.8 | 36.60 | 90.4 |
| 3 days | 31.42 | 77.6 | 38.91 | 96.1 |

EXAMPLE 4

Testing Effect of Fermentation Time on the Process

Crushed bone with a phosphorus content of 2.2% and organic matter content of 27% was used in these experiments. Crushed bone was fermented with S1 bacteria population for 3, 5, 7 and 10 days at 50° C. according to the procedure described in Example 3, above Fermentation broths were filtered as a warm suspension by suction filtration with a 140 μm (micrometer) wire mesh. Fermented crushed bone was washed with warm water (60° C.) until the washing liquor remained clear. After fermentation and washing procedure, 32-34 w-% (weight percent) of the starting material remained, which indicates removal of organic matter up to 73.4%. Table XVIII shows the organic matter contents and phosphorus contents for fermented crushed bone for each fermentation time period. Practically no phosphorus was lost during the fermentation step. This was confirmed by spectrophotometric analysis of the phosphorus content of the fermentation liquor, according to the procedure described in Example 1, and in addition, by analyzing the phosphorus content after fermentation according to Table XVIII. The results indicate that longer fermentation times (5, 7 and 10 days) do not further diminish the amount of organic matter.

TABLE XVIII

Organic matter content and phosphorus content of the fermented crushed bone after different fermentation times. *)Calculated from wet material. The composition of crushed bone and fermented crushed bone were analysed by Novalab, Karkila, Finland.

| Ferementation time, days | Removed organic matter after fermentation, % | Phosphorus content after fermentation, %* |
|---|---|---|
| 3 | 70.9 | 6.8 |
| 5 | 73.4 | 5.5 |
| 7 | 69.3 | 5.8 |
| 10 | 69.1 | 6.8 |

Fermentation results were further examined with shorter fermentation times. Fermentation was performed with with S1 bacteria inoculate according to procedure described in Example 3. Crushed bone was fermented for different times, and then subjected to solubilization using citric and sulfuric acid. The Fermentation step was performed according to the procedure described in Example 3, above, with following quantities, 240 g of crushed boric was weighed in six bottles, 330 ml tap water was added to each bottle and mixed, 30 ml of bacterial inoculum was added to each mixture and was mixed, 260 g of crushed bone was weighed in six bottles, 357.5 ml of tap water was added to each bottle and the mixtures were shaken, 32.5 ml of bacterial inoculum was added to each mixture. The fermentation times (the incubation time) were 3, 6, 10, 12, 14, 16, 18, 24, 30, 48, 54 and 72 hours. After the desired incubation time had elapsed, two of the bottles (240 g and 260 g of crushed bone) were filtered arid washed with warm tap water (60° C.) until the washing water was clear. The composition of the fermented crushed bone matrix is presented in Table XIII(b). Total amount of phosphorus was 2.2% of the material (crushed bone). One organic and one inorganic acid were chosen for these solubilization tests based an the above previous results. The acids used were Citric and sulfuric acid. The preparation of these two acids is shown in a table below.

TABLE XIX

Making the citric acid solutions in milli-Q water.

| Mass of acid per 1 kg of solids, g | Amount of acid, g | Volume of acid solution, ml |
|---|---|---|
| 150 | 7.5 | 100 |

TABLE XX

Making the sulfuric acid solutions milli-Q water.

| Mass of acid per 1 kg of solids, g | Amount of 100% acid, g | Volume of used acid, ml | Volume of water, ml | Volume of water, ml |
|---|---|---|---|---|
| 150 | 7.5 | 4.29 | 95.71 | 100 |

Summary selection of acid dissolving with citric acid and sulfuric acid after different fermentation times is presented in Table XXI.

TABLE XXI

Concentration of dissolved phosphates in g/l from different fermented crushed bone (FBC) using citric and sulfuric acid as dissolving acids.

| Acid | Amount of acid per 1 kg *BC (g) | Time of fermentation (h) | Concentration of dissolved phosphate (g/l) | Time of acid treatment |
|---|---|---|---|---|
| Citric acid (150 g/l) | 100 | 3 | 14.3 ± 0.3 | 4 h |
| | | 6 | 14.3 ± 0.5 | |
| | | 10 | 20.7 ± 0.7 | |
| | | 12 | 28.1 ± 2.8 | |
| | | 14 | 33.6 ± 1.6 | |
| | | 16 | 32.5 ± 3.6 | |
| | | 18 | 20.7 ± 0.8 | |
| | | 24 | 22.0 ± 0.8 | |
| | | 30 | 25.8 ± 1.0 | |
| | | 48 | 23.9 ± 1.3 | |
| | | 54 | 27.2 ± 2.2 | |
| | | 72 | 35.4 ± 1.5 | |
| Citric acid (150 g/l) | 100 | 3 | 17.5 ± 0.2 | 7 h |
| | | 6 | 19.0 ± 0.2 | |
| | | 10 | 26.2 ± 1.1 | |
| | | 12 | 37.1 ± 3.2 | |
| | | 14 | 33.5 ± 0.3 | |
| | | 16 | 35.5 ± 0.2 | |
| | | 18 | 41.7 ± 2.5 | |
| | | 24 | 41.6 ± 2.6 | |
| | | 30 | 44.8 ± 2.2 | |
| | | 48 | 37.6 ± 5.1 | |
| | | 54 | 42.0 ± 4.8 | |
| | | 72 | 44.6 ± 0.6 | |
| Citric acid (150 g/l) | 100 | 3 | 27.9 ± 0.8 | 24 h |
| | | 6 | 27.4 ± 1.3 | |
| | | 10 | 39.6 ± 0.7 | |
| | | 12 | 52.4 ± 2.4 | |
| | | 14 | 54.3 ± 4.0 | |
| | | 16 | 45.1 ± 6.5 | |
| | | 18 | 72.1 ± 6.4 | |

TABLE XXI-continued

Concentration of dissolved phosphates in g/l from different fermented crushed bone (FBC) using citric and sulfuric acid as dissolving acids.

| Acid | Amount of acid per 1 kg *BC (g) | Time of fermentation (h) | Concentration of dissolved phosphate (g/l) | Time of acid treatment |
|---|---|---|---|---|
| | | 24 | 53.3 ± 3.2 | |
| | | 30 | 68.5 ± 5.7 | |
| | | 48 | 62.5 ± 6.1 | |
| | | 54 | 66.4 ± 5.7 | |
| | | 72 | 71.6 ± 3.3 | |
| Citric acid (150 g/l) | 100 | 3 | 44.1 ± 1.9 | 2 d |
| | | 6 | 34.9 ± 3.8 | |
| | | 10 | 55.3 ± 7.8 | |
| | | 12 | 61.1 ± 2.7 | |
| | | 14 | 44.8 ± 0.4 | |
| | | 16 | 56.2 ± 0.5 | |
| | | 18 | 54.8 ± 7.0 | |
| | | 24 | 62.8 ± 6.1 | |
| | | 30 | 83.0 ± 7.7 | |
| | | 48 | 88.8 ± 4.5 | |
| | | 54 | 79.0 ± 2.6 | |
| | | 72 | 83.1 ± 4.8 | |
| Sulfuric acid (150 g/l) | 100 | 3 | 22.4 ± 0.8 | 4 h |
| | | 6 | 25.2 ± 1.3 | |
| | | 10 | 43.4 ± 0.1 | |
| | | 12 | 46.6 ± 2.3 | |
| | | 14 | 56.0 ± 3.9 | |
| | | 16 | 48.3 ± 3.8 | |
| | | 18 | 49.6 ± 2.0 | |
| | | 24 | 53.8 ± 5.7 | |
| | | 30 | 44.2 ± 3.2 | |
| | | 48 | 44.0 ± 6.6 | |
| | | 54 | 47.5 ± 5.5 | |
| | | 72 | 50.1 ± 3.9 | |
| Sulfuric acid (150 g/l) | 100 | 3 | 23.6 ± 0.9 | 7 h |
| | | 6 | 25.0 ± 0.9 | |
| | | 10 | 42.5 ± 1.8 | |
| | | 12 | 45.5 ± 4.3 | |
| | | 14 | 49.6 ± 0.9 | |
| | | 16 | 55.4 ± 0.7 | |
| | | 18 | 57.7 ± 2.7 | |
| | | 24 | 57.5 ± 8.1 | |
| | | 30 | 59.8 ± 4.3 | |
| | | 48 | 53.4 ± 4.6 | |
| | | 54 | 69.8 ± 3.6 | |
| | | 72 | 64.3 ± 1.2 | |
| Sulfuric acid (150 g/l) | 100 | 3 | 26.3 ± 1.7 | 24 h |
| | | 6 | 27.3 ± 0.3 | |
| | | 10 | 50.4 ± 2.0 | |
| | | 12 | 45.1 ± 1.4 | |
| | | 14 | 49.6 ± 4.6 | |
| | | 16 | 64.0 ± 5.5 | |
| | | 18 | 73.9 ± 9.4 | |
| | | 24 | 70.6 ± 1.1 | |
| | | 30 | 70.9 ± 4.9 | 5 |
| | | 48 | 69.9 ± 1.9 | |
| | | 54 | 77.1 ± 2.8 | |
| | | 72 | 74.4 ± 2.8 | |
| Sulfuric acid (150 g/l) | 100 | 3 | 33.7 ± 1.3 | 2 d |
| | | 6 | 35.9 ± 1.6 | |
| | | 10 | 67.6 ± 3.2 | |
| | | 12 | 64.5 ± 4.0 | |
| | | 14 | 52.1 ± 1.6 | |
| | | 16 | 57.4 ± 3.6 | |
| | | 18 | 68.0 ± 4.5 | 10 |
| | | 24 | 64.1 ± 7.3 | |
| | | 30 | 70.9 ± 1.2 | |
| | | 48 | 72.9 ± 1.0 | |
| | | 54 | 68.0 ± 3.1 | |
| | | 72 | 67.5 ± 8.3 | |
| Sulfuric acid (150 g/l) | 100 | 3 | 36.4 ± 0.2 | 7 d |
| | | 6 | 40.9 ± 0.3 | |
| | | 10 | — | |
| | | 12 | 68.1 ± 6.4 | 15 |
| | | 14 | 80.0 ± 11.6 | |
| | | 16 | 80.7 ± 10.5 | |

TABLE XXI-continued

Concentration of dissolved phosphates in g/l from different fermented crushed bone (FBC) using citric and sulfuric acid as dissolving acids.

| Acid | Amount of acid per 1 kg *BC (g) | Time of fermentation (h) | Concentration of dissolved phosphate (g/l) | Time of acid treatment |
|------|------|------|------|------|
| | | 18 | 80.0 ± 4.3 | |
| | | 24 | 73.3 ± 5.6 | |
| | | 30 | — | |
| | | 48 | 71.9 ± 5.1 | |
| | | 54 | 80.8 ± 13.1 | |
| | | 72 | 87.4 ± 4.2 | |

*BC is crushed bone

The above results clearly show that the recovery of phosphorus increases after fermentation times of over 10 hours, compared to shorter fermentation times. In addition, the amount of phosphorus recovered remained at the same level with fermentation times of 10-72 hours, which indicated that a sufficient time for fermentation can be as low as 10 hours with selected acid and bone containing material.

Figure 5:
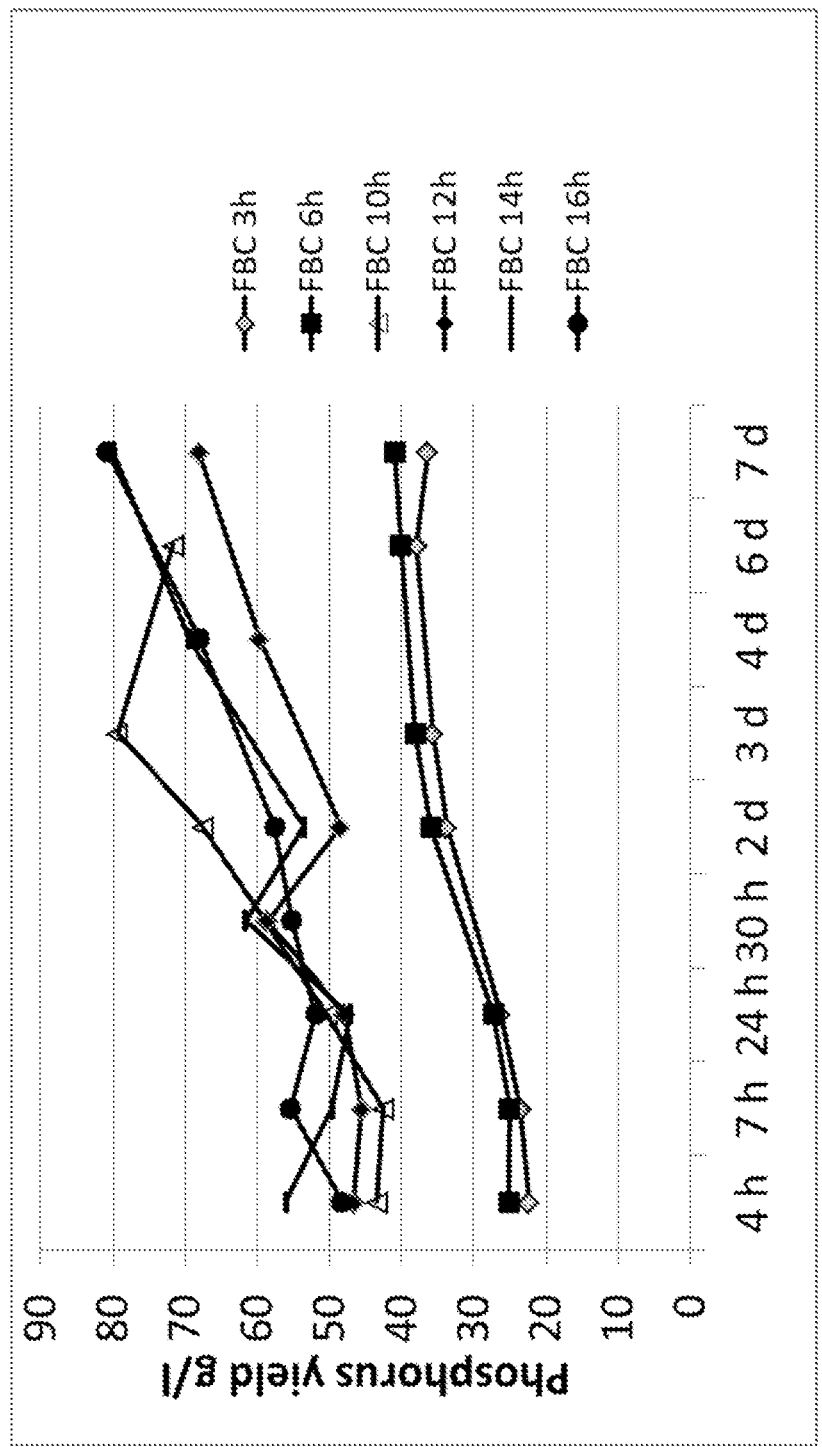
FIG. 5 Illustrates phosphate recovery as g/l with different times (3, 6, 10, 12, 14, 16*h* fermented crushed bone when sulfuric acid is used as a dissolving acid.

The amount of organic matter present in crushed bone materials that were fermented for five different time periods (6, 18, 24, 48, 72 h) was analyzed at Novalab (Karkkila, Finland). Analysis indicated that all samples contained 35-39% of organic matter, in dry weight, that indicated similar removal of organic matter with all fermentation times of 18 h, 24, 48 h and 72 hours. This proves that a sufficient fermentation time for removal of organic matter is 18 hours or less. Table XXII shows the results of solids removal during different fermentation times, and also gives analysis data for organic matter and phosphorus content. FIG. 5 also clearly shows that shorter fermentation times of 3 and 6 hours produces a lower yield of dissolved phosphate. According to the results, sufficient time for the fermentation step is 12-18 hours.

TABLE XXII

Removal of solids during fermentation with S1 bacteria population. In addition, analysis data obtained from Novalab (Karkkila, Finland) in regards of organic matter and phosphorus content

| Fermentation time, h | Crushed bone remained after fermentation, % | Organic matter in dry weight % | Removed organic matter during fermentation, % | Phosphorus content after fermentation, % |
|------|------|------|------|------|
| 3 | 79.8 | — | — | — |
| 6 | 78.1 | 56 | 15.6 | 2.5 |
| 10 | 38.2 | — | — | — |
| 12 | 33.1 | 36 | 63.6 | 6.4 |
| 14 | 30.7 | — | — | — |
| 16 | 33.2 | — | — | — |
| 18 | 33.2 | 36 | 63.3 | 6.1 |
| 24 | 35.4 | 37 | 57.4 | 5.6 |
| 30 | 32.7 | — | — | — |
| 48 | 33.9 | 35 | 62.7 | 5.8 |
| 54 | 33.1 | — | — | — |
| 72 | 31.9 | 39 | 70.9 | 5.8 |

EXAMPLE 5

Solubilization of Nonfermented Crushed Bone in Acid at Temperatures of 50° C.

Solubilization of phosphorus was tested at two different temperatures in Example 5. The crushed bone used in these experiments contained 2.7% phosphorus, 28.9% nitrogen, 31% organic matter and 53.8% moisture. The used acids were chosen based on the previous experiments and based on the prices of the acids. The acids included in these experiments were citric, L-(+)-lactic and formic acid. The acid concentrations were 2% (w/w) and 5% (w/w) of acid in the reaction mixture (w/w refers to weight/weight). The temperatures tested were 50° C. and 95° C. The experiments were conducted in the following manner: 80 g of crushed bone vas weighed in glass bottles. Different acid solutions of 200 ml were made according to Tables XXIII and XXIV. Acids were preheated to the temperatures 50° C. and 95° C. before adding each acid solution to one of the bottles containing crushed bone. The experiments were conducted according to the same procedure as the experiments in Example 1. The results are presented in Table XXV. Based on the results it seems that high temperatures do not bring benefits for the process, therefore lower temperatures can be used.

Table XXIII Making the citric acid solutions in milli-Q water. The total volume

TABLE XXIII

Making the citric acid solutions in milli-Q water. The total volume of the acid solution was 200 ml.

| Mass percent of acid in reaction mixture, % | Amount of acid, g | Concentration of acid solution, g/l |
|------|------|------|
| 2 | 5.6 | 28 |
| 5 | 14.0 | 70 |

TABLE XXIV

Making the acid solutions of the liquid acids in milli-Q water. The total volume of each acid solution was 200 ml. The density of 98% formic acid was 1.22 kg/l and the density of 85% L-(+)-lactic acid was 1.206 kg/l.

| Acid | Mass percent of acid in reaction mixture, % | Amount of 100% acid, g | Volume used acid, ml | Volume of water, ml | Concentration of acid solution, g/l |
|------|------|------|------|------|------|
| 98% Formic acid | 2 | 5.6 | 4.7 | 195.3 | 28 |
| | 5 | 14.0 | 11.7 | 188.3 | 70 |
| 85% L-(+)-Lactic acid | 2 | 5.6 | 5.5 | 194.5 | 28 |
| | 5 | 14.0 | 13.7 | 186.3 | 70 |

TABLE XXV

The results of solubilization of phosphorus from crushed bone at elevated temperatures

| Acid | Mass percent of acid in reaction mixture, % | Amount of acid per 1 kg BC, g | Conditions of acid treatment | Concentration of dissolved phosphate g/l | Yield of dissolved phosphorus % |
|------|------|------|------|------|------|
| Citric acid | 2 | 70 | 50° C., 7 h | 6.26 | 18.9 |
| | 5 | 175 | 50° C., 7 h | 11.78 | 35.6 |
| | 2 | 70 | 95° C., 7 h | 5.19 | 15.7 |
| | 5 | 175 | 95° C., 7 h | 14.18 | 42.8 |

TABLE XXV-continued

The results of solubilization of phosphorus
from crushed bone at elevated temperatures

| Acid | Mass percent of acid in reaction mixture, % | Amount of acid per 1 kg BC, g | Conditions of acid treatment | Concentration of dissolved phosphate g/l | Yield of dissolved phosphorus % |
|---|---|---|---|---|---|
| L-(+)- Lactic acid | 2 | 70 | 50° C., 7 h | 3.85 | 11.1 |
| | 5 | 175 | 50° C., 7 h | 11.08 | 33.5 |
| | 2 | 70 | 95° C., 7 h | 1.51 | 4.5 |
| | 5 | 175 | 95° C., 7 h | 5.30 | 16.0 |
| Formic acid | 2 | 70 | 50° C., 7 h | 7.90 | 23.8 |
| | 5 | 175 | 50° C., 7 h | 14.98 | 45.2 |
| | 2 | 70 | 95° C., 7 h | 3.60 | 10.9 |
| | 5 | 175 | 95° C., 7 h | 8.47 | 25.6 |

EXAMPLE 6

Solubilization of Fermented Crushed Bone in Acid with Different Fermentation Times at Temperatures of 37° C. and 70° C.

Crushed bone materials, fermented with S1 bacteria population for 3, 5, 7 and 10 days, as described in Example 3, were further treated with 3% and 5% citric, formic and sulfuric acid solutions at 37° C. and 70° C. Fermented crushed bone of 40° g and 100 ml of each acid solution were added to 24 different 250 ml glass bottles. The amount of acid was calculated as a percentage based on the whole reaction mixture. The bottles were shaken vigorously at start and placed in a water bath or an incubator. Samples (1 ml) were taken after 4, 7, 24 and 30 h, and in some cases experiments were continued for several days. Before each sampling, the reaction mixtures were thoroughly shaken. Samples were centrifuged and the separated liquid supernatant was spectrophotometrically analyzed for phosphate(Synergy H1 Reader) according to the procedure described in Example 1, above. The results are presented in Table XXVI. The phosphorus solubilization ability of the tested acids diminished in the following order: sulfuric acid>citric acid>formic acid. The highest recovery percent was observed after 4 and 7 h. The percentage of phosphorus recovery with sulfuric acid was reduced after 4 h treatment. A fermentation time of 3 days proved to be sufficient. Longer fermentation times did not yield better phosphorus recovery. High temperature treatment did not improve the recovery of phosphorus. The highest phosphor is recovery was observed by treating with 5% sulfuric acid for 30 h at 37° C. and for 4 h at 70° C., yielding phosphorus recovery percentages of 49% and 39%, respectively.

EXAMPLE 7

Phosphorus Dissolution by Different Acids at 10° C. and Room Temperature for Fermented Crushed Bone Crushed bone was fermented for 3 days at 50° C. in an incubator according to Example 3. Fermented bone was treated with 3% and 5% citric, formic, DL-malic and sulfuric acid solutions according to procedure described in Example 2. The results are presented in Table XXII. More concentrated acid solutions of 5% gave up to 50% higher recovery rates than 3% acid solutions, at both room temperature (RT) and at 10° C. 24 hour treatment with 5% sulfuric acid and 5% DL-Malic acid at RT gave yields of 57% and 45%, respectively. A summary of the results is presented in the Table XXII.

TABLE XXVI

Phosphorus recovery (%) with acid treatments of sulfuric, citric, formic, DL-malic and L-(+)-lactic acid at different temperatures.

| | Temperature | | | |
|---|---|---|---|---|
| Acid | 10° C. | RT | 37° C. | 70° C. |
| Sulfuric acid 3% | | | | |
| 4 h | 23.3 | 24.7 | 23.5 | 22.4 |
| 7 h | 25.3 | 27.4 | 24.3 | 21.2 |
| 24 h | 19.3 | 21.6 | 17.9 | 15.9 |
| 30 h | 18.3 | 17.5 | 18.1 | 18.2 |
| 48 h | 19.0 | 16.1 | 14.9 | 15.9 |
| 3 d | 14.5 | 14.2 | — | — |
| 6 d | 17.4 | 14.3 | — | — |
| Sulfuric acid 5% | | | | |
| 4 h | 33.9 | 38.3 | 38.3 | 40.3 |
| 7 h | 49.7 | 47.9 | 47.2 | 38.7 |
| 24 h | 43.8 | 56.8 | 44.2 | 31.3 |
| 30 h | 44.7 | 48.1 | 49.1 | 33.8 |
| 48 h | 45.4 | 52.1 | 44.4 | 29.0 |
| 3 d | 41.4 | 53.4 | — | — |
| 6 d | 32.5 | 37.1 | — | — |
| Citric acid 3% | | | | |
| 4 h | 6.2 | 11.1 | 10.5 | 12.9 |
| 7 h | 13.8 | — | 12.9 | 13.8 |
| 24 h | 17.2 | 15.3 | 14.5 | — |
| 30 h | 13.9 | 19.8 | 17.5 | 15.6 |
| 48 h | 19.7 | 14.5 | 15.6 | 16.9 |
| 3 d | 18.3 | 13.0 | — | — |
| 6 d | 19.7 | 11.6 | — | — |
| Citric acid 5% | | | | |
| 4 h | 20.4 | 24.4 | 20.6 | 22.7 |
| 7 h | 27.6 | 27.1 | 20.6 | 25.4 |
| 24 h | 37.9 | 30.4 | 34.5 | 17.0 |
| 30 h | 34.9 | 38.2 | 29.7 | 16.7 |
| 48 h | 38.7 | 28.8 | 22.9 | 15.1 |
| 3 d | 29.7 | 22.9 | — | — |
| 6 d | 23.0 | 21.1 | — | — |
| Formic acid 3% | | | | |
| 4 h | 9.1 | 14.0 | 26.3 | 16.5 |
| 7 h | 20.7 | 16.3 | 22.4 | 13.4 |
| 24 h | 7.8 | 4.9 | 7.3 | 4.0 |
| 30 h | 5.0 | 4.6 | 8.5 | 4.6 |
| 48 h | 3.1 | 3.0 | 5.8 | 5.9 |
| 3 d | 2.8 | 3.8 | — | — |
| 6 d | 1.8 | 3.1 | — | — |
| Formic acid 5% | | | | |
| 4 h | 23.9 | 27.1 | 17.5 | 9.6 |
| 7 h | 25.8 | 30.0 | 14.3 | 9.3 |
| 24 h | 15.2 | 11.8 | 3.2 | 4.0 |
| 30 h | 12.3 | 9.9 | 3.3 | 5.5 |
| 48 h | 10.0 | 8.3 | 2.4 | 5.2 |
| 3 d | 14.7 | 7.7 | — | — |
| 6 d | 8.6 | 11.0 | — | — |

TABLE XXVI-continued

Phosphorus recovery (%) with acid treatments of sulfuric, citric, formic, DL-malic and L-(+)-lactic acid at different temperatures.

| Acid | Temperature | | | |
|---|---|---|---|---|
| | 10° C. | RT | 37° C. | 70° C. |
| DL-Malic acid 3% | | | | |
| 4 h | 21.3 | 20.8 | — | — |
| 7 h | 10.9 | 14.0 | — | — |
| 24 h | 13.8 | 16.3 | — | — |
| 30 h | 13.9 | 16.8 | — | — |
| 48 h | 18.8 | 21.4 | — | — |
| DL-Malic acid 5% | | | | |
| 4 h | 29.2 | 28.4 | — | — |
| 7 h | 27.2 | 26.3 | — | — |
| 24 h | 31.1 | 45 | — | — |
| 30 h | 32.7 | 37.1 | — | — |
| 48 h | 34.3 | 24.8 | — | — |
| L-(+)-Lactic acid 3% | | | | |
| 4 h | 5.4 | 7.6 | — | — |
| 7 h | 7.0 | 6.3 | — | — |
| 24 h | 7.9 | 6.6 | — | — |
| 30 h | 8.0 | 6.2 | — | — |
| 48 h | 5.2 | 4.0 | — | — |
| L-(+)-Lactic acid 5% | | | | |
| 4 h | 18.0 | 19.7 | — | — |
| 7 h | 17.4 | 22.4 | — | — |
| 24 h | 9.1 | 13.2 | — | — |
| 30 h | 7.0 | 9.1 | — | — |
| 48 h | 3.8 | 5.8 | — | — |

Comparing Acid Concentrations at Room Temperature

Figure 3:
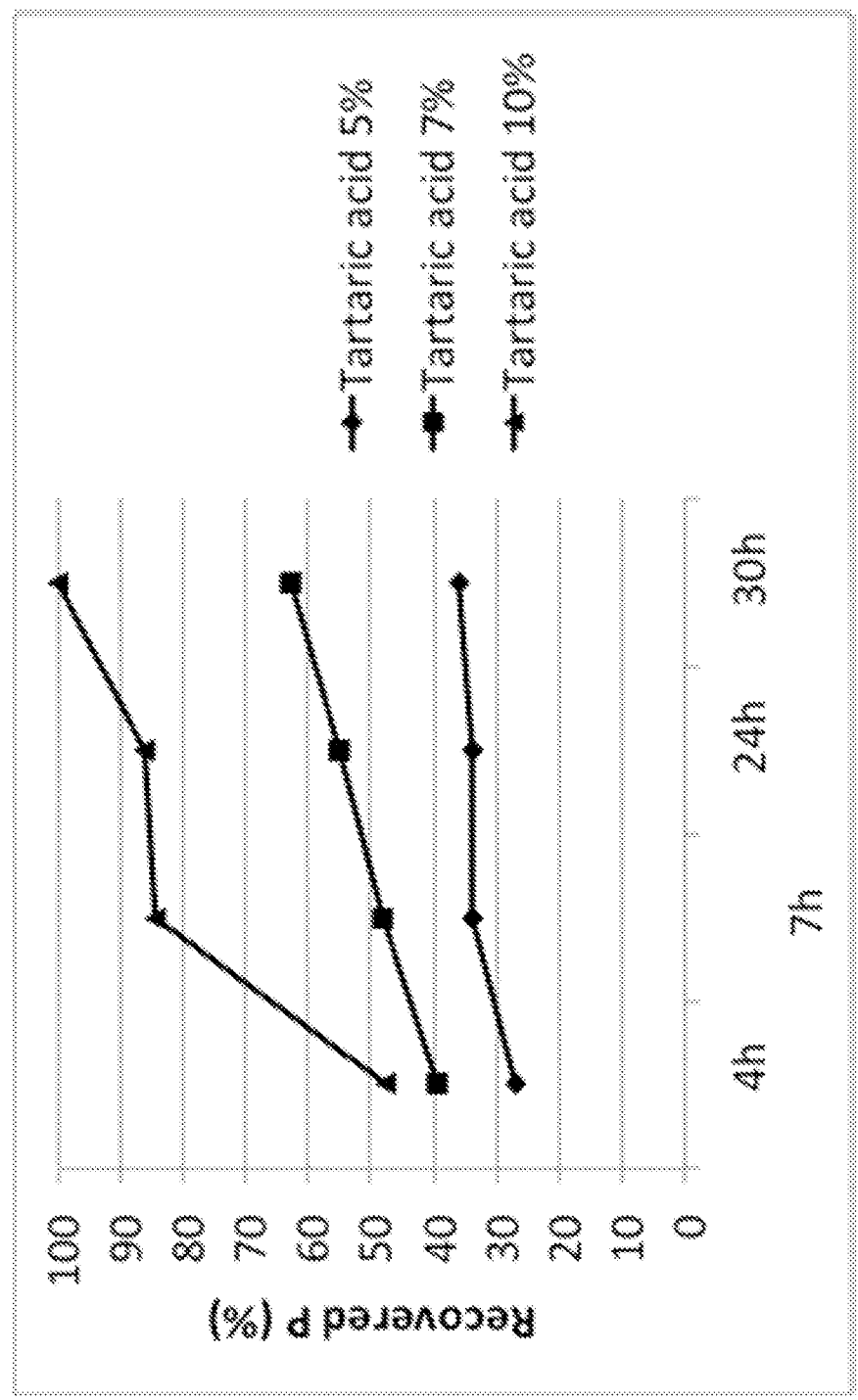
FIG. 3 illustrates treatment of fermented crushed bone with 5%, 7% and 10% tartaric acid concentrations (calculated as mass percentages in the whole reaction mixture) at room temperature.

Crushed bone was fermented similarly according to the Example 3, 5%, 7% and 10% acid solutions of citric, tartaric, DL-malic, and sulfuric acid were used to acid dissolution experiments. Results presented in Table XXVII. Effect of different concentration (5%, 7%, 10%) of tartaric acid at room temperature are presented in FIG. 3 for clarity purposes to illustrate effect of acid concentration to the yield.

TABLE XXVII

Recovery of phosphorus with different acid concentrations.

| Recovery of Phosphorus (%) | 4 h | 7 h | 24 h | 30 h |
|---|---|---|---|---|
| Citric acid 5% | 25.3 | 25.7 | 30.0 | 42.6 |
| Citric acid 7% | 19.1 | 54.3 | 39.3 | 58.1 |
| Citric acid 10% | 29.7 | 41.3 | 76.4 | 75.2 |
| Tartaric acid 5% | 27 | 33.9 | 33.9 | 36.0 |
| Tartaric acid 7% | 39.3 | 48.2 | 55.0 | 62.7 |
| Tartaric acid 10% | 47.5 | 84.3 | 86.2 | 99.9 |
| DL-Malic acid 5% | 20.6 | 24.3 | 37.6 | 42.3 |
| DL-Malic acid 7% | 26.9 | 32.3 | 59.0 | 57.7 |
| DL-Malic acid 10% | 32.1 | 44.9 | 62.7 | 75.6 |
| Sulphuric acid 5% | 31.0 | 48.0 | 53.9 | 40.2 |
| Sulphuric acid 7% | 29.5 | 49.0 | 67.6 | 66.4 |
| Sulphuric acid 10% | 48.9 | 60.6 | 86.5 | 86.4 |

Further tests were conducted with citric acid, malic acid and mixtures thereof, according to the procedure described in Example 2, above, at room temperature. First, the crushed bone was subjected to fermentation according to Example 3, above with S1 bacteria population. Acid concentrations or 8.5 and 10% were used, and each sample had a biological replicate. The acid dissolving stage was continued for 7 days and the samples were analyzed for released phosphate after 4, 7, 24, 30 h and 3 d, 4d and 7 d. The results are presented in Table XXVII. The result is an average of two biological replicates, and the error bars show the standard deviations of three replicate spectrophotometric phosphate measurement.

TABLE XXVIII

Recovery of phosphorus with citric acid, malic acid and their mixture.
Recovery of Phosphorus (%)

| | 4 h | 7 h | 24 h | 30 h | 3 d | 4 d | 7 d |
|---|---|---|---|---|---|---|---|
| Citric acid 8.5% | 20.3 ± 1.8 | 26.3 ± 0.8 | 66.6 ± 6.3 | 81.5 ± 5.2 | 82.4 ± 8.6 | 87.3 ± 2.4 | 70.0 ± 5.1 |
| Citric acid 10% | 24.5 ± 9.8 | 33 ± 3.5 | 80 ± 3.2 | 86.3 ± 10.0 | 99.7 ± 0.7 | 99.8± | 92.7 ± 8.3 |
| DL-Malic acid 8.5% | 21.9 ± 1.5 | 30.4 ± 2.4 | 45.4 ± 8.1 | 86.3 ± 3.1 | 86.0 ± 10.3 | 90.3± | 71.0 ± 2.7 |
| DL-Malic acid 10% | 28.7 ± 4.4 | 35.7 ± 3.6 | 64.5 ± 6.7 | 99.5 ± 5.2 | 89.3 ± 4.2 | 89.6 ± 8.7 | 61.1 ± 8.5 |
| Mixture of Citric acid 4.25% and DL-Malic acid 4.25% | 18.9 ± 1.8 | 28.7 ± 3.6 | 39.0 ± 4.3 | 51.4± | 46.4 ± 3.3 | 54.1 ± 1.9 | 55.2 ± 5.4 |
| Mixture of Citric acid 5% and DL-Malic acid 5% | 26.4 ± 1.3 | 34.6 ± 5.7 | 44.3 ± 4.1 | 54.5 ± 4.1 | 58.9 ± 8.8 | 61.3 ± 9.1 | 59.1 ± 3.9 |

Citric acid gave over 80% yields with both acid concentrations of 8.5% and 10%. Malic acid gave also high yields of dissolved phosphorus after 30 h treatment time. An acid concentrations of 8.5% and 10% correlates to 120 g/l and 140 g/l acid solutions, respectively. However, mixture of citric acid and malic acid gave much lower recovery yields as seen in Table XXVIII. Results show that citric acid and malic acid with concentrations of 8.5-10%(w/w) are excellent options to dissolve phosphorus from bone containing material.

EXAMPLE 8

Optimizing the Ratio of the Bone Feedstock and Water in the Acid Solubilization of Phosphorus The mass of the fermented crushed bone and the amount of the acid were the same in each experiment, but the volume of the water where the acid as dissolved was changed in the different experiments. The crushed bone used in these experiments contained 2.2% phosphorus, 25.9% nitrogen, 27% organic matter and 60.7% moisture. 1.8 k of crushed bone was weighed in a bucket, 2,475 l tap water W as added to the bucket, followed by mixing. The resulting mixture was preheated to 50° C. in an incubator. Then a 225 ml S1 bacterial inoculum was added to the mixture, followed by mixing. The fermentation step was conducted as described in Example 3, above. After the 1.8 kg of crushed bone had been fermented, vacuum filtrated and washed, only 36.1% of the solid crushed bone remained. 40 g of the fermented crushed bone Was weighed into 14 glass bottles, and each of the 14 samples was mixed with the acid solutions, prepared according to Tables XXIX and XXX. The experiments were conducted at room temperature according to the same procedure as detailed by Example above. The results are presented in Tables XXXI and XXXII.

TABLE XXIX

Making the citric acid solutions for the experiments to optimize the ratio of the fermented crushed bone and the amount of water where the acid is dissolved. After making the acid solutions in milli-Q water each of the solutions was mixed with 40 g of the fermented crushed bone.

| Acid | Amount of acid, g | Total volume of acid solution, ml |
|---|---|---|
| Citric acid | 14 | 40 |
|  |  | 60 |
|  |  | 80 |
|  |  | 120 |
|  |  | 140 |
|  |  | 160 |

TABLE XXX

Making the sulfuric acid solutions for the experiments to optimize the ratio of the fermented crushed bone fermented with S1 bacteria population and the amount of water where the acid is dissolved. After the acid solutions were prepared in milli-Q water, each of the solutions was mixed with 40 g of the fermented crushed bone.

| Acid | Amount of 100% acid, g | Volume of 95% acid solution, ml | Volume of water, ml | Total volume of acid solution, ml |
|---|---|---|---|---|
| 95% Sulfuric acid | 14 | 8.009 | 31.991 | 40 |
|  |  |  | 51.991 | 60 |
|  |  |  | 71.991 | 80 |
|  |  |  | 111.991 | 120 |
|  |  |  | 131.991 | 140 |
|  |  |  | 151.991 | 160 |

TABLE XXXI

The results of the experiments to optimize the ratio of the fermented crushed bone and the amount of water where the citric acid is dissolved. 126 g of citric acid was added per 1 kg of crushed hone. The yield of the dissolved phosphorus was determined as a mass percent of the phosphorus content of the crushed bone

| Total volume of acid solution, ml | Time of acid treatment, h | Concentration of dissolved phosphate, g/l | Yield of dissolved phosphorus, % |
|---|---|---|---|
| 40 | 4 | 61.38 | 32.9 |
|  | 7 | 89.56 | 47.9 |
|  | 24 | 144.54 | 77.4 |
| 60 | 4 | 43.84 | 35.2 |
|  | 7 | 61.33 | 49.2 |
|  | 24 | 107.89 | 86.6 |
| 80 | 4 | 38.41 | 41.1 |
|  | 7 | 58.64 | 62.8 |
|  | 24 | 81.36 | 87.1 |
| 100 | 4 | 22.63 | 29.7 |
|  | 7 | 31.47 | 41.3 |
|  | 24 | 58.24 | 76.4 |
| 120 | 4 | 25.14 | 40.4 |
|  | 7 | 32.81 | 52.7 |
|  | 24 | 50.15 | 80.5 |
| 140 | 4 | 21.08 | 39.5 |
|  | 7 | 30.22 | 56.6 |
|  | 24 | 45.25 | 84.8 |
| 160 | 4 | 18.94 | 40.6 |
|  | 7 | 21.48 | 46.0 |
|  | 24 | 32.63 | 69.9 |

TABLE XXXII

The results of the experiments to optimize the ratio of the fermented crushed bone and the amount of water, where the sulfuric acid is dissolved. The amount of the sulfuric acid was 126 g per 1 kg crushed bone. The yield of the dissolved phosphorus was determined as a mass percent of the phosphorus content of the crushed bone.

| Total volume of acid solution, ml | Time of acid treatment, h | Concentration of dissolved phosphate, g/l | Yield of dissolved phosphorus, % |
|---|---|---|---|
| 40 | 4 | 52.11 | 27.9 |
|  | 7 | 107.45 | 57.5 |
|  | 24 | 124.20 | 66.5 |
| 60 | 4 | — | — |
|  | 7 | 72.88 | 58.5 |
|  | 24 | 91.86 | 73.8 |
| 80 | 4 | — | — |
|  | 7 | 53.42 | 57.2 |
|  | 24 | 84.60 | 90.6 |
| 100 | 4 | 37.27 | 48.9 |
|  | 7 | 46.17 | 60.6 |
|  | 24 | 65.91 | 86.5 |
| 120 | 4 | 40.46 | 65.0 |
|  | 7 | 40.36 | 64.8 |
|  | 24 | 44.86 | 72.0 |
| 140 | 4 | 35.08 | 65.7 |
|  | 7 | 35.36 | 66.2 |
|  | 24 | 43.56 | 81.6 |
| 160 | 4 | 24.38 | 52.2 |
|  | 7 | 29.25 | 62.6 |
|  | 24 | 32.59 | 69.8 |

Based on the above results, an 80 ml acid solution per 40 g of fermented crushed bone game the highest recovery.

EXAMPLE 9

Solubilization of Fermented Crushed Bone Using Crushed Lemon

Solubilization of phosphorus from fermented crushed one (fermented with S1 bacteria population) using crushed lemon was tested in two different temperatures. Room temperature (RT) was chosen based on previous results showing that higher temperatures did not give any advantages in solubilization of phosphorus. A temperature of 10° C. was chosen to prove that lower temperatures will not affect the rate of solubilization of phosphorus from fermented crushed bone. The experiments were done in the following manner: Lemon was crushed in a mixer, and mixtures containing 5% and 30% (w/w%) of lemon were made according to Table XXXIIII. The mixture of lemon and water used at lower temperature was cooled first to 10° C. 40 g of fermented crushed bone was weighed in glass betties. Each lemon mixture was added to one bottle containing fermented crushed bone. The results are presented in Table XXIV.

TABLE XXXIII

Making the lemon mixtures in milli-Q water. The total volume of each mixture was 100 ml.

| Number of experiment | Concentration of lemon in reaction mixture, % | The mass of lemon, g | Concentration of lemon mixture, g/l |
|---|---|---|---|
| 1 | 5 | 7 | 70 |
| 2 | | | |
| 3 | 30 | 42 | 420 |
| 4 | | | |

TABLE XXXIV

The results of solubilization of phosphorus from fermented crushed bone using crushed lemon.

| Number of experiment | Amount of lemon per 1 kg of BC, g | Conditions of acid treatment | Concentration of dissolved phosphate g/l | Yield of dissolved phosphorus |
|---|---|---|---|---|
| 1 | 59.5 | RT, 6d | 0.12 | 0.1 |
| 2 | 360.0 | 10° C., 6d | 0.76 | 1.0 |
| 3 | 62.7 | RT, 6d | 4.38 | 5.7 |
| 4 | 375.9 | 10° C., 6d | 8.18 | 10.6 |

Based on the results of these experiments, the ability of lemon to dissolve phosphorus was found to be limited.

EXAMPLE 10

Other Waste Materials

Phosphorous containing materials were tested without fermentation and after fermentation with S1 bacteria inoculate according to a procedure described in Example 3. The tested materials were: minced food waste, fish by-product, minced chicken by-product, minced broiler by-products, feather meal, and bovine skin material. The phosphorus contents are presented in Table XXXV.

TABLE XXXV

Phosphorus content of different materials analyzed by Novalab (Karkkila, Finland)

| Phosphorus content of different waste materials (%) | |
|---|---|
| Fish by-product | 0.7 |
| Broiler by-product | 0.75 |
| Minced chicken by-product | 1.6 |
| Ground feathers | 0.33 |
| Minced food waste | 0.5 |

Unfermented waste material. Two biological replicate samples of minced food waste (50 g) were weighed in a glass bottle and 100 ml of citric acid solution and 100 ml of sulfuric acid solution were added to the parallel samples. Acid solutions contained 15 g of acid per 100 ml solution. This means 300 g of acid/1 kg of waste material. The same procedure was repeated using different waste materials. The phosphates were measured spectrophotometrically (Synergy H1 Reader) using a Malachite green phosphate assay kit (POMG-25H, BioAssay Systems) according to the manufacturer's instructions. Phosphate amounts were measured spectrophotometrically after 1 d, 2 d and 1 week. Bovine skin gave a very small recovery of phosphorus. Recovery percentages of phosphorus from the different materials are presented in Table XXXV1. The result is an average of two biological replicates and the error bars show the standard deviations of three replicate spectrophotometric phosphate measurement.

It was clear that fish and chicken based waste materials gave the highest phosphorus yields. These materials were chosen for further examinations.

TABLE XXXVI

| Phosphorus recovery from different waste material | P Yield after 2 d (%) Citric acid 300 g/l kg waste material | Sulfuric acid 300 g/l kg waste material |
|---|---|---|
| Minced food waste | 8.5 ± 1.3 | 9.3 ± 0.4 |
| Fish by-product | 60.9 ± 1.3 | 68.6 ± 1.4 |
| Broiler by-product | 72.2 ± 1.2 | 76.9 ± 2.0 |
| Minced chicken by-product | 78.1 ± 1.0 | 79.7 ± 1.0 |
| Ground feather | 19.5 ± 0.7 | 12.8 ± 0.5 |

Fermented waste material. Two biological replicate samples of minced chicken by-products were weighed (120 g) to glass bottles. 165 ml of tap water and 15 ml of S1 bacterial inoculate was added to the mixture. The mixtures were incubated at 50° C. for 18 hours. After incubation time the bottles were opened in a laminar flow hood to release the formed gases. Further, the bottles were heat-treated at 95° C. for an hour to inactivate the added bacteria inoculate. Thereafter, the mixture was filtered with 100 μm wire mesh filter and solids were washed with warm water (60° C.). After fermentation and washing procedure, 28% of solids were recovered from minced chicken by-product. Gained solids were subjected to acid dissolving stage with sulfuric acid. Acid solutions contained 14 g of acid per 100 ml solution (140 g/l). Acid amount was 117 g of acid/l kg of the original waste material and 350 g of acid per fermented waste material. Phosphate amounts were measured (kit) after 4, 7 24 h and 2 d. Results are presented in Table XXXVII. The result is an average of two biological replicates and the error bars show the standard deviations of three replicate spectrophotometric phosphate measurement.

TABLE XXXVII

Phosphorus recovery from unfermented and fermented minced chicken by-product

| Acid | Sample | Time | P yield % | P g/l |
|---|---|---|---|---|
| Citric Acid (140 g/l) | Minced Chicken by-product (unfermented) | 4 h | 31.3 ± 1.0 | 6.0 ± 0.6 |
| | | 7 h | 32.8 ± 4.9 | 6.3 ± 2.9 |
| | | 24 h | 44.6 ± 4.8 | 8.6 ± 2.8 |
| | | 2 d | 47.0 ± 8.7 | 7.5 ± 2.2 |
| Citric Acid (140 g/l) | Fermented minced Chicken by-product (fermented with S1 bacteria population) | 4 h | 56.3 ± 5.2 | 10.8 ± 3.1 |
| | | 7 h | 57.4 ± 5.8 | 11.0 ± 3.4 |
| | | 24 h | 67.5 ± 9.6 | 13.0 ± 3.9 |
| | | 2 d | 79.8 ± 8.7 | 15.3 ± 3.9 |

According to the results phosphorus can be recovered from bone containing chicken based waste materials. Phosphorus recovery from fermented chicken waste material was 79.8% that means 15.3 g per liter of phosphorus. However, unfermented chicken material gave only 47% yield (7.5 g/l P).

EXAMPLE 11

Production of Biofertilizer

Ammonia as a gas phase was directed from ammonia containing liquor, produced from the fermentation step, into a bottle containing a liquid derived from solubilization of crushed bone by sulfuric acid. Ammonia was removed as a gas from our bioreactor by increasing the pH and temperature, and by aerating the bioreactor contents, which converts the ammonium-ions into ammonia gas (the ammonia was stripped from the liquor).

Crushed bone was first fermented for three days at 50° C. after which the solids were separated from the liquid by filtration. The solids, i.e., fermented and separated crushed bone, was solubilized for 17 hours using sulfuric acid, after which the solids were separated from the liquid by filtration. The filtered liquid was then used as "a trap liquid" which absorbed the gaseous ammonia. The trap liquid contained 0.62 g/kg ammonium nitrogen ($NH_4$-N) before stripping and 5.3 g/kg ammonium nitrogen ($NH_4$-N) alter stripping/absorbing. The nitrogen content increased almost nine fold during the stripping stage. As a result, a biofertilizer liquor containing both ammonium and phosphates was formed. It was also observed that valuable micronutrients, in addition to phosphorus, were extracted from the organic waste material during the acid treatment stage. Analysis (Novalab) of the obtained biofertilizer liquor showed that liquor typically contains small amounts of calcium, magnesium, boron, chlorine, copper, iron, manganese, molybdenum and zinc.

EXAMPLE 12

Comparative Fermentations

Comparative fermentations with water and two different bacteria inoculates (S1 and soil population) were performed. Composition of the S1 mixed bacterial population is presented in table XIII(a) and the soil mixed bacterial population was created by mixing non-sterile forest soil with boiling tap water in a proportion of 180 g of soil per liter of water. Crushed bone (crushed bovine and porcine bones) were used as a fresh waste material in this experiment. Crushed bone samples of 120 grams were weighed, and tap water (or tap water and bacteria inoculum), was added to samples. 180 ml of water was added to zero (0) samples (controls) and 165 ml of water and 15 ml of bacteria inoculate 5% (v/v) to inoculated samples. Samples were treated at room temperature (RT) or 50° C. for a period of 16 hours. After incubation time, the samples were hygienized at 95° C. water bath for an hour this is sufficient time and temperature to kill vegetative bacteria). Solids were filtered through 140 μm wire mesh and washed with hot water (60° C.). Ammonia yields were measured from filtrates using enzymatic determination kit for ammonia (Ammonia Assay Kit AA0100; Sigma-Aldrich). Washed solids were subjected to an acid dissolving stage with 100 ml of citric acid (140 g/l) per each sample during 24 hours. Results of the experiment are presented in table XXXVIII.

TABLE XXXVIII

Crushed bone treated with or without bacteria inoculum at RT and 50° C.

| Sample | Bacteria inoculate | Temp. (° C.) | Ammonia yield (mg/l) after 16 h | Mass removed during fermentation (%) | P yield (%) after 24 h | Dissolved phosphorus after 24 h (g/l) |
|---|---|---|---|---|---|---|
| BC | — | RT | 89.8 ± 44 | 23.3 | 59.6 ± 0.8 | 15.7 ± 2.8 |
| BC | S1 | RT | 471.9 ± 191 | 28.6 | 58.6 ± 6.2 | 15.5 ± 4.1 |
| BC' | — | 50 | 118.6 ± 87 | 39.2 | 51.8 ± 3.4 | 13.6 ± 4.4 |
| BC | S1 | 50 | 3625.5 ± 345 | 68.6 | 91.8 ± 1.8 | 24.4 ± 4.5 |
| BC (sterilized) | — | 50 | 101.4 ± 24 | 28.3 | 38.7 ± 2.7 | 10.2 ± 2.6 |
| BC (sterilized) | S1 | 50 | 3419.9 ± 225 | 75.1 | 47.2 ± 3.3 | 12.5 ± 1.9 |
| BC | FI1 | 50 | 766.5 ± 33 | 63.2 | 58.2 ± 4.5 | 15.4 ± 1.2 |

BC is bone crush or crushed bone

Results showed that S1 gives much higher yields of ammonia than plain water or the forest soil inoculum FI1 after 16 hours of treatment at 50° C. In addition, the amount of dissolved phosphates was 24.4 g/l (91.8% yield) after a 24 hour treatment time with S1 mixed bacteria population. However, samples treated with tap water or forest soil bacteria inoculum provided dissolved phosphate yields of 15.5 g/ and 15.4 g/l, respectively.

Discussion

Based on the results presented herein, it is clear that there are advantages provided by fermenting bone material before phosphorus solubilization. The advantages of fermenting bone material before phosphorus solubilization with acid treatment include a) the reduced consumption of acid used for the solubilization reaction and b) the removal of bone's organic matter which could potentially form explosive compounds with the solubilizing acid. Table XXXIV illustrates selected results from the various examples.

Acid treatment experiments of fermented crushed bone have clearly showed that phosphorus can be recovered in high yields from bone with several organic acids, such as tartaric acid, malic acid, citric acid, as well as with an inorganic acid, such as sulfuric acid. Nearly 100% recovery yield of phosphorus could be recovered with 10% tartaric acid after 30 hours at room temperature. in addition, 10% sulfuric acid yielded 86% after 30 h at room temperature. Tartaric acid is a Fermented crushed bone could be treated at 10-70° C. temperatures for 4 hours to several days depending on the temperature and solubilization acid. Preferably, room temperature is used at the acid solubilization stage.

Bath organic and inorganic acids can be used to solubilize phosphorus from bone material. However, organic acids are less corrosive than strong mineral acids. The solubilization reaction may be accelerated by higher temperatures, however, side reactions also start to occur at higher temperatures. For example, solubilized phosphate also solubilizes Calcium ions into the acid solution and these can start to react with acids forming soluble or insoluble precipitates depending on the used acid.

TABLE XXXIX

Summary. The highest yields with different acids and concentrations.

| Acid | Acid concentration % | Amount of acid per 1 kg crushed bone | Treatment conditions | Concentration of dissolved phosphate g/l | Concentration of dissolved phosphorus g/l | Yield of dissolved phosphorus % |
|---|---|---|---|---|---|---|
| Citric acid | 3 | 35.8 | RT, 30 h | 15.3 | 5.0 | 19.8 |
| | 5 | 59.7 | RT, 30 h | 29.5 | 9.6 | 38.2 |
| | 7 | 83.5 | RT, 30 h | 44.3 | 14.5 | 58.1 |
| | 10 | 119.3 | RT, 30 h | 57.3 | 18.7 | 75.1 |
| Sulfuric acid | 3 | 35.8 | RT, 7 h | 21.2 | 6.9 | 27.4 |
| | 5 | 59.7 | RT, 24 h | 44.8 | 14.6 | 57.9 |
| | 7 | 83.5 | RT, 24 h | 51.5 | 16.8 | 67.6 |
| | 10 | 119.3 | RT, 24 h | 65.9 | 21.5 | 86.5 |
| Formic acid | 3 | 35.8 | 37° C., 4 h | 12.6 | 4.1 | 16.3 |
| | 5 | 59.5 | RT, 7 h | 23.4 | 7.6 | 30.3 |
| L-(+)-Lactic acid | 3 | 37.6 | 10° C., 24 h | 6.1 | 2.0 | 7.9 |
| | 5 | 62.7 | 10° C., 7 h | 17.4 | 5.7 | 22.4 |
| Tartaric acid | 5 | 62.0 | RT, 30 h | 27.4 | 8.9 | 36.0 |
| | 7 | 86.7 | RT, 30 h | 47.8 | 15.6 | 62.7 |
| | 10 | 123.9 | RT, 30 h | 76.2 | 24.8 | 100.0 |
| DL-malic acid | 5 | 62.0 | RT, 30 h | 32.2 | 10.5 | 42.3 |
| | 7 | 86.7 | RT, 24 h | 45.0 | 14.7 | 59.0 |
| | 10 | 123.9 | RT, 30 h | 57.6 | 18.8 | 75.6 | highly interesting option tor the phosphorus solubilization stage of the process, since it is produced as a by-product of wine industry. Also, citric acid, malic acid and lactic acid are interesting and sustainable options for phosphorus solubilization since they can be produced biotechnically.

Room temperature proved to be a suitable reaction temperature. Elevated temperatures did not improve the yields obtained from phosphorus dissolution from bone.

Interestingly, the selection of solubilization acid was bone material dependent. For example, for MBM, a different set of acids might be better than for bone crush (BC) and fermented BC. In addition, dissolution times were found to be function of material under treatment.

Based on embodiments phosphorus dissolution consists of two steps 1) fermentation of crushed bone material to remove organic matter and thereafter 2) treatment of fermented crushed bone with acid at different conditions to dissolve phosphorus into soluble phosphates. This two-step process results in a dissolved phosphate solution that can be used, after optional neutralization, as a biofertilizer. In general, phosphate containing crushed bone is fermented up to three (3) days and thereafter treated with organic acid, such as citric, tartaric, malic, lactic acid or with inorganic acid such as sulfuric acid.

According to an embodiment 3-10% acid solution, such as tartaric acid, citric acid, sulfuric acid, can be used as a solubilization acid. Preferably, 7-10% acid concentration is used.

Figure 4:
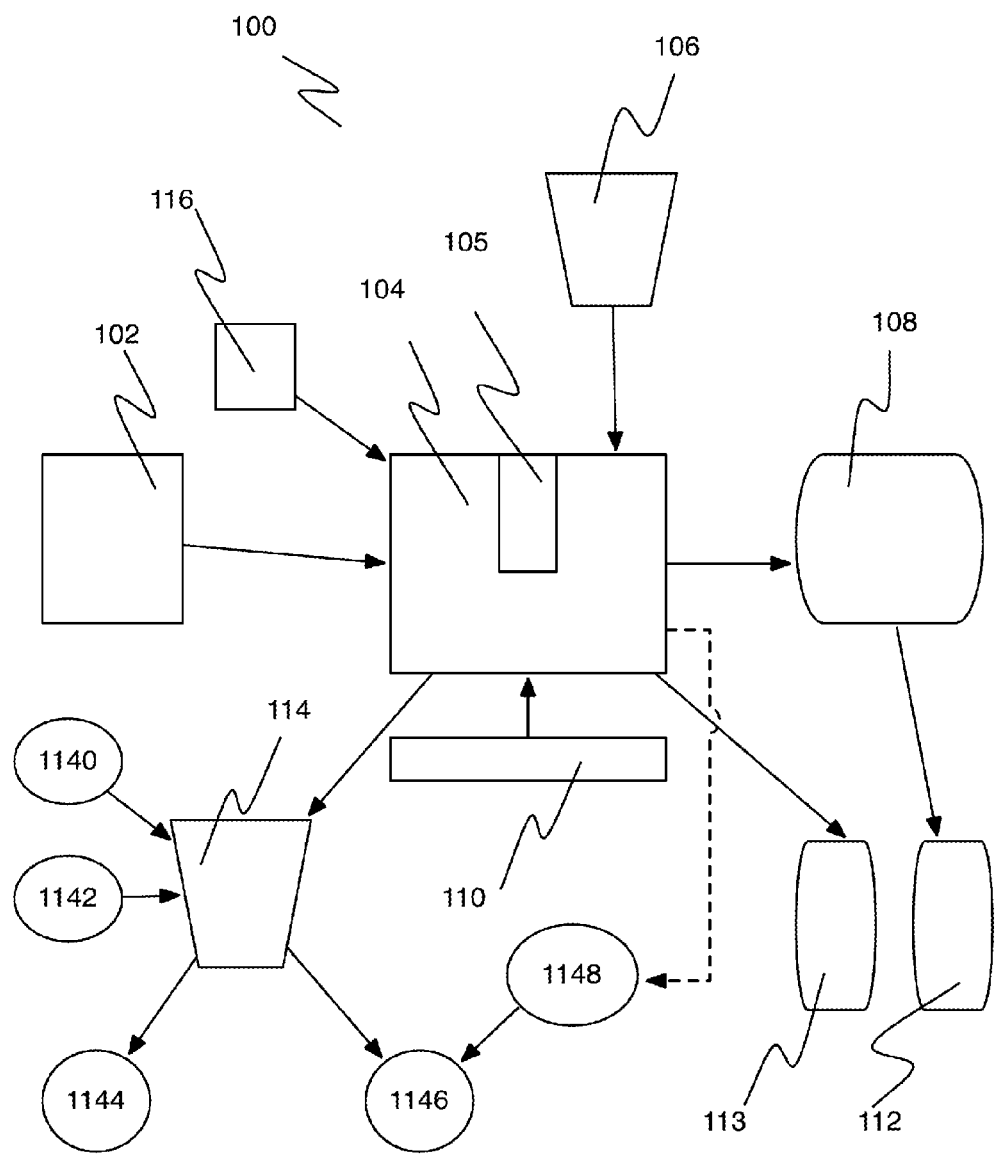
FIG. 4 illustrates an example embodiment according to present disclosure.

An example environment 100 of a phosphorus recovery/harvesting/collection process from bone containing material is shown in FIG. 4. The bone containing material is stored in a container 106. The bones are preferably crushed to approximately 0-5 mm particle size. The crushed bone in the container 106 is fed to as bioreactor 104. Water is added to the bioreactor 104 from a water source 102. Bacteria or mixed bacterial population (inoculum) is added to the bioreactor 104 from a source 116. The type of inoculum is selected preferably from group consisting of ammonification capable microorganisms. Examples of such bacteria are disclosed in co-owned U.S. patent application Ser. No. 13/722,228, filed on Dec. 20, 2012, incorporated herein by reference in its entirety. Preferably the inoculum is from a mixed population of bacteria as disclosed by co-owned U.S. application Ser. No. 14/066,089, filed on Oct. 29, 2013, the contents of which are incorporated by reference herein its entirety.

In a preferred aspect, the bioreactor includes mixing/stirring means 105 and heating/temperature controlling means 110. According to certain embodiments, heating, element 110 is used to heat the content of the bioreactor 104 to about 50 degrees Celsius, depending on the selected microorganisms. If needed, the pH can be controlled by adding a base (such as NaOH) to the bioreactor 104 to keep the pH at levels of over 6. Fermentation time is preferably about 3 days.

During the fermentation process using mixed bacterial population ammonium/ammonia is released to fermentation liquid. Samples of the liquid from the bioreactor 104 can be taken from time to time to follow the progress of the process. A parameter to follow is ammonia/ammonium concentration within the liquid. The fermentation process is complete or sufficient when change of the concentration between two consequence samples does not demonstrate significant increase.

The fermentation product of solids and liquid are treated with separate processes according to following procedures. All or some of the liquid from the bioreactor 104 can be led to stripping phase 108 where ammonium/ammonia is extracted as ammonia ($NH_3$) from the liquid. The ammonia can be stored in a container 112 for future use such as a part of fertilizer production. Alternatively some or all of the liquid can be led to container 113 and used directly as fertilizer. Alternatively, some or all of the liquid can be used in a precipitation process as indicated with dashed line.

After removing all or some of the liquid the remaining solids can be collected in a container 114. Water from source 1140 and acids from source 1142 are added to the container. Alternatively, a ready acid solution can be used. The acid solution (acid/water mixture) results in dissolution of phosphorous from the solids to the liquid. Depending on the usage the liquid that contains phosphorous as phosphates can be collected to container 1144 and used as fertilizer either directly or after adjusting pH level. Alternatively, or additionally, the liquid can be collected to container 1146 for precipitation purposes. Precipitation can be done, for example, by adding an $NH_4^-$ liquid from 1148 and $Mg^{2+}$ ions containing solution to the container 1146.

Precipitation refers to the formation of a solid in a solution during a chemical reaction. When the reaction occurs in a liquid, the solid formed is called the precipitate. The chemical that causes the solid to form is called the precipitant. In case of forming phosphorus (P) containing precipitate $NH_4^+$ containing liquid and $Mg^{3+}$ ions containing solution are used as precipitants.

INCORPORATION BY REFERENCE

Numerous references are cited throughout this application, each of which is incorporated by reference herein in its entirety.

CLAIM OF BENEFIT

This application claims the benefit of U.S. Provisional Application Ser. No. 61/790,927, filed on Mar. 15, 2013, the contents of which are incorporated herein by reference in their entirety.

REFERENCES

CN102020508A, Preparation and application method of water-soluble humic acid inorganic compound fertilizer, 2011

Dowd, S.E., Wolcott, R.D., Sun, Y., McKeehan, T., Smith, E., Rhoads, D. 2008a. Polymicrobial nature of chronic diabetic foot ulcer biofilm infections determined using bacterial tag encoded FLX amplicon pyrosequencing (bTEFAP). *PLoS ONE* 3(10): e3326.

Dowd, S.E., Sun, Y., Secor, P.R., Rhoads, D.D., Wolcott, B.M., James, G.A., Wolcott, R.D. 2009b. Survey of bacterial diversity in chronic wounds using Pyrosequencing, DGGE, and full ribosomes shotgun sequencing. *BMC Microbiology* 8: 43.

Grech, Nigel, M., EP 1964828B1. Method of generating, phosphorus fertilizers through the utilization of microbial fermentation technology, 2010

Ringelberg, David, B., US6,776,816 B1, Methods for accelerating production of magnesium ammonium phosphate while attaining higher yileds thereof and a slow-release fertilizer produced therefrom, 2004

Wolcott, R., Gontcharova, V., Sun, Y., Dowd, S.E. 2009. Evaluation of the bacterial diversity among and within individual venous leg ulcers using bacterial tag-encoded FLX and Titanium amplicon pyrosequencing and metagenomic approaches, *BMC Microbiology* 9: 226.

Woodruff, Steven R., US 6,464,875 B1, Food, animal, vegetable and food preparation byproduct treatment apparatus and process, 2002

We claim:

1. A process for producing phosphate from an organic material, wherein the organic material comprises bone suitable for extraction of phosphates, comprising:
   (a) fermenting the organic material in a medium in the presence of at least one microorganism, wherein the fermenting is under conditions, and for a sufficient period of time, to produce a fermentation product;
   (b) treating solids of the fermentation product with acid, in a medium to solubilize phosphates from the fermentation product,
   wherein the solids of the fermentation product comprises the bone suitable for extraction of phosphates;
   (c) separating a liquid phase from the acid treated fermentation product;
   (d) admixing a reagent comprising $NH_4^+$ and/or a reagent comprising $Mg^{2+}$ ions into the separated liquid phase in a sufficient amount and for a period of time sufficient to precipitate solubilized phosphates from the separated liquid phase; and
   (e) recovering the precipitated phosphate.

2. The process of claim 1 wherein the at least one microorganism is a bacteria capable of ammonification.

3. The process of claim 1 further comprising co-producing ammonia or ammonium during fermenting step (a).

4. The process of claim 1 wherein the acid is an organic acid or an inorganic acid.

5. The process of claim 4 wherein the acid is selected from group consisting of tartaric acid, malic acid, citric acid, sulfuric acid and combinations thereof.

6. The process of claim 1 wherein the precipitated phosphate is struvite or magnesium ammonium phosphate.

7. The process of claim 1 wherein the fermenting step is conducted with an inoculum of microorganisms ranging in dose from 1 to 20 vol-%.

8. The process of claim 7 wherein the fermenting step is conducted with an inoculum of microorganisms ranging in dose from 5 to 10 vol-%.

9. The process of claim 1 wherein the fermenting step is conducted at a temperature ranging from 30 to 60° C.

10. The process of claim 9 wherein the fermenting step is conducted at a temperature ranging from 40 to 55° C.

11. The process of claim 1 wherein the fermenting step is conducted for a time ranging from 10 hours to 7 days.

12. The process of claim 11 wherein the fermenting step is conducted for a time ranging from 12 hours to 18 hours.

13. The process of claim 1 wherein the acid solubilization step is conducted at a pH ranging from 1 to 6.

14. The process of claim 13 wherein the acid solubilization step is conducted at a pH ranging from 2 to 3.

15. The process of claim 1 wherein the acid solubilization step if conducted for a time ranging from 15 minutes to 14 days.

16. The process of claim 15 wherein the acid solubilization step is conducted for a time ranging from 7 hours to 48 hours.

17. The process of claim 1 wherein the fermentation process is conducted with an organic material ranging in density from 10 to 50 g/100 ml wt/vol of medium.

18. The process of claim 17 wherein the fermentation process is conducted with an organic material ranging in density from 20 to 40 g/100 ml wt/vol of medium.

19. The process of claim 1 wherein the medium is an aqueous medium.

20. The process of claim 1, wherein the at least one microorganism is a mixed bacterial population that has a correlation coefficient of at least 0.90 relative to a mixed bacterial population selected from the group consisting of S1, FI1 and FO2.

* * * * *